US011701253B2

(12) United States Patent
Black et al.

(10) Patent No.: US 11,701,253 B2
(45) Date of Patent: Jul. 18, 2023

(54) SYSTEMS, DEVICES AND METHODS INCLUDING GALVANIC AND CALORIC VESTIBULAR STIMULATION

(71) Applicant: Scion NeuroStim, Inc., Durham, NC (US)

(72) Inventors: Robert D. Black, Chapel Hill, NC (US); Lanty L. Smith, Durham, NC (US); Lesco L. Rogers, Raleigh, NC (US)

(73) Assignee: Scion NeuroStim, Inc., Durham, NC (US)

(*) Notice: Subject to any disclaimer, the term of this patent is extended or adjusted under 35 U.S.C. 154(b) by 144 days.

(21) Appl. No.: 17/315,542

(22) Filed: May 10, 2021

(65) Prior Publication Data
US 2021/0259879 A1    Aug. 26, 2021

Related U.S. Application Data

(63) Continuation of application No. 15/914,516, filed on Mar. 7, 2018, now Pat. No. 11,026,835, which is a
(Continued)

(51) Int. Cl.
*A61F 7/12*    (2006.01)
*A61N 1/04*    (2006.01)
(Continued)

(52) U.S. Cl.
CPC ................ *A61F 7/12* (2013.01); *A61B 6/037* (2013.01); *A61F 7/007* (2013.01); *A61M 21/02* (2013.01);
(Continued)

(58) Field of Classification Search
CPC ............. A61B 6/037; A61F 2007/0005; A61F 2007/0075; A61F 2007/0093;
(Continued)

(56) References Cited

U.S. PATENT DOCUMENTS 4,711,243 A    12/1987  Schafer
6,374,143 B1    4/2002  Berrang et al.
(Continued)

FOREIGN PATENT DOCUMENTS

CN    87203225 U    12/1987
CN    1572336 A    2/2005
(Continued)

OTHER PUBLICATIONS

Second Office Action corresponding to Chinese Application No. 201680062001.6, dated Aug. 20, 2020, 15 pages.
(Continued)

*Primary Examiner* — Amanda K Hulbert
(74) *Attorney, Agent, or Firm* — Myers Bigel, P.A.

(57) ABSTRACT

A vestibular neurostimulation device, which may include first and second electrodes; first and second thermoelectric devices thermally coupled, respectively, to first and second earpieces that are configured to be insertable into respective ear canals of a patient; and a controller comprising a waveform generator. The waveform generator may be is configured to deliver a modulated electric signal to the patient through galvanic vestibular stimulation (GVS) using the first and second electrodes and to deliver a time varying thermal waveform to the patient through caloric vestibular stimulation (CVS) using the first and second earpieces simultaneous with the delivery of the modulated electrical signal through GVS. The CVS and/or GVS may be configured to increase a passage of insulin-like growth factor 1 (IGF-1) through a blood-brain-barrier.

20 Claims, 19 Drawing Sheets

Related U.S. Application Data continuation-in-part of application No. PCT/US2016/049824, filed on Sep. 1, 2016, and a continuation-in-part of application No. PCT/US2016/049827, filed on Sep. 1, 2016, and a continuation-in-part of application No. PCT/US2016/049836, filed on Sep. 1, 2016.

(60) Provisional application No. 62/322,985, filed on Apr. 15, 2016, provisional application No. 62/214,474, filed on Sep. 4, 2015.

(51) Int. Cl.
| | |
|---|---|
| A61N 1/36 | (2006.01) |
| A61B 6/03 | (2006.01) |
| A61N 1/05 | (2006.01) |
| A61F 7/00 | (2006.01) |
| A61M 21/02 | (2006.01) |
| H04R 1/10 | (2006.01) |
| A61M 21/00 | (2006.01) |
| A61N 1/32 | (2006.01) |

(52) U.S. Cl.
CPC ......... *A61N 1/0456* (2013.01); *A61N 1/0484* (2013.01); *A61N 1/0526* (2013.01); *A61N 1/36021* (2013.01); *A61N 1/36025* (2013.01); *A61N 1/36028* (2013.01); *A61N 1/36031* (2017.08); *A61N 1/36034* (2017.08); *H04R 1/1016* (2013.01); *H04R 1/1091* (2013.01); *A61F 2007/0005* (2013.01); *A61F 2007/0075* (2013.01); *A61F 2007/0093* (2013.01); *A61F 2007/126* (2013.01); *A61M 2021/0027* (2013.01); *A61M 2021/0072* (2013.01); *A61M 2021/0077* (2013.01); *A61M 2205/054* (2013.01); *A61M 2210/0662* (2013.01); *A61N 1/327* (2013.01); *H04R 1/10* (2013.01); *H04R 2460/13* (2013.01)

(58) Field of Classification Search
CPC ...... A61F 2007/126; A61F 7/007; A61F 7/12; A61M 2021/0027; A61M 2021/0072; A61M 2021/0077; A61M 21/02; A61M 2205/054; A61M 2210/0662; A61N 1/0456; A61N 1/0484; A61N 1/0526; A61N 1/327; A61N 1/36021; A61N 1/36025; A61N 1/36028; A61N 1/36031; A61N 1/36034; H04R 1/10; H04R 1/1016; H04R 1/1091; H04R 2460/13
See application file for complete search history.

(56) References Cited

U.S. PATENT DOCUMENTS

| | | |
|---|---|---|
| 7,420,465 B2 | 9/2008 | Ritter |
| 7,856,275 B1 | 12/2010 | Paul et al. |
| 8,696,724 B2 | 4/2014 | Rogers |
| 10,207,101 B2 | 2/2019 | Galea et al. |
| 10,918,518 B2 | 2/2021 | Black et al. |
| 2003/0195588 A1 | 10/2003 | Fischell et al. |
| 2007/0150027 A1 | 6/2007 | Rogers |
| 2007/0299895 A1 | 12/2007 | Johnson et al. |
| 2008/0300519 A1 | 12/2008 | Helt et al. |
| 2009/0082831 A1 | 3/2009 | Zachary et al. |
| 2010/0010564 A1 | 1/2010 | Simon |
| 2010/0114187 A1 | 5/2010 | Wood et al. |
| 2010/0211142 A1 | 8/2010 | Rogers et al. |
| 2011/0313499 A1 | 12/2011 | Smith et al. |
| 2012/0016431 A1 | 1/2012 | Paul et al. |
| 2012/0130465 A1 | 5/2012 | Risi et al. |
| 2012/0316624 A1 | 12/2012 | Smith et al. |
| 2013/0090520 A1 | 4/2013 | Redfield et al. |
| 2013/0303953 A1 | 11/2013 | Lattner |
| 2015/0005840 A1 | 1/2015 | Pal et al. |
| 2015/0148878 A1 | 5/2015 | Yoo et al. |
| 2015/0222999 A1 | 8/2015 | Rasmussen et al. |
| 2015/0328461 A1 | 11/2015 | Charlesworth et al. |
| 2015/0360030 A1 | 12/2015 | Cartledge et al. |
| 2016/0228771 A1 | 8/2016 | Watson |

FOREIGN PATENT DOCUMENTS

| | | |
|---|---|---|
| CN | 101773702 B | 10/2012 |
| CN | 104220128 A | 12/2014 |
| CN | 104382668 A | 3/2015 |
| JP | S62501192 A | 5/1987 |
| JP | 2014507964 A | 4/2014 |
| WO | 8602567 A1 | 5/1986 |
| WO | 2006085401 A1 | 8/2006 |
| WO | 2009039294 A1 | 3/2009 |
| WO | 2010135783 A1 | 12/2010 |
| WO | 2011161562 A1 | 12/2011 |
| WO | 2013071307 A1 | 5/2013 |
| WO | 2013134873 A1 | 9/2013 |
| WO | 2014118094 A1 | 8/2014 |
| WO | 2014134564 A1 | 9/2014 |

OTHER PUBLICATIONS

"International Preliminary Report on Patentability, corresponding to International Application No. PCT/US2016/049827, dated Mar. 6, 2018, 8 pp."

"International Preliminary Report on Patentability, corresponding to International Application No. PCT/US2016/049836, dated Mar. 6, 2018, 8 pp."

"International Search Report and Written Opinion of the International Searching Authority, corresponding to International Application No. PCT/US2016/049824, dated Mar. 13, 2017, 17 pgs."

"Notice of Reasons for Refusal, Japanese Patent Application No. 2018-511600 and Machine Translation thereof, dated Oct. 26, 2020 (7 pages)".

"Notice of Reasons for Refusal, Japanese Patent Application No. 2018-511750 and Machine Translation thereof, dated Oct. 26, 2020 (6 pages)".

"Office Action corresponding to Chinese Application No. 201680062001.6, dated Nov. 5, 2019".

"R. C. Fitzpatrick, B. L. Day, Probing the human vestibular system with galvanic stimulation. J Appl Physiol 96, 2301-2316 (2004); published online EpubJune (10.1152/japplphysiol.00008.2004)".

Black, et al., ""Non-lnvasive Neuromodulation Using Time-Varying Caloric Vestibular Stimulation," IEEE Neurovascular Devices and Systems, vol. 4, 2016".

De Hemptinne C, , et al., ""Therapeutic deep brain stimulation reduces cortical phase-amplitude coupling in Parkinson's disease," Nature Neuroscience, vol. 8, 779-786 (2015)".

Fukushima A, , et al., ""Frequencies of Inaudible High-Frequency Sounds Differentially Affect Brain Activity: Positive and Negative Hypersonic Effects," PLoS ONE, vol. 9, issue 4, e95464 (Apr. 2014)".

G. C. Albert, , et al., ""Deep brain stimulation, vagal nerve stimulation and transcranial stimulation: An overview of stimulation parameters and neurotransmitter release". Neurosci Biobehav Rev 33, 1042-1060 (2009); published online EpubJuly (10.1016/j.neubiorev.2009.04.006)".

J. Rosell, , et al., ""Skin impedance from 1 Hz to 1 MHz," IEEE Trans Biomed Eng 35, 649-651 (1988); published online EpubAugust (10.1109/10.4599)".

Kim DJ, , et al., ""Noisy Galvanic Vestibular Stimulation Modulates the Amplitude of EEG Synchrony Patterns," PLoS ONE, vol. 8, issue 7, e69055 (Jul. 2013)".

Krawinkel LK, , et al., ""Modulating pathological oscillations by rhythmic non-invasive brain stimulation—a therapeutic concept?", first published online at http://biorxiv.org/content/early/2015/01/29/014548 (Jan. 29, 2015), also published in Front. Syst. Neurosci. (Mar. 1".

(56) References Cited

OTHER PUBLICATIONS

M. W. Bagnall, , et al., ""Frequency-independent synaptic transmission supports a linear vestibular behavior," Neuron 60, 343-352 (2008); published online EpubOct. 23 (S0896-6273(08)00845-3 [pii] 10.1016/j.neuron.2008.10.002)".

Welgampola MS, , et al., ""Vestibular activation by bone conducted sound," J Neurol Neurosurg Psychiatry, 74:771-778 (2003)".

Translation of Portion of Chinese Reexamination Notification corresponding to CN 201680062001.6; dated Nov. 1, 2022 (9 pages, English translation only).

Bent, Leah R., et al., "Modulation of muscle sympathetic bursts by sinusoidal galvanic vestibular stimulation in human subjects", Experimental Brain Research, 174, 2006, 701-711.

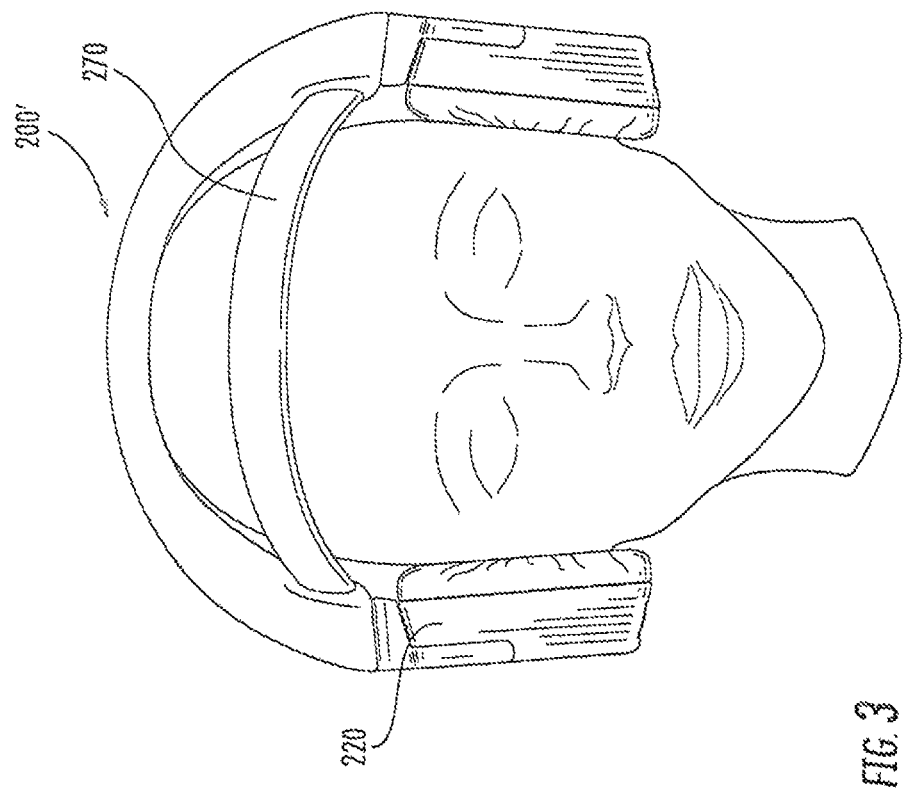
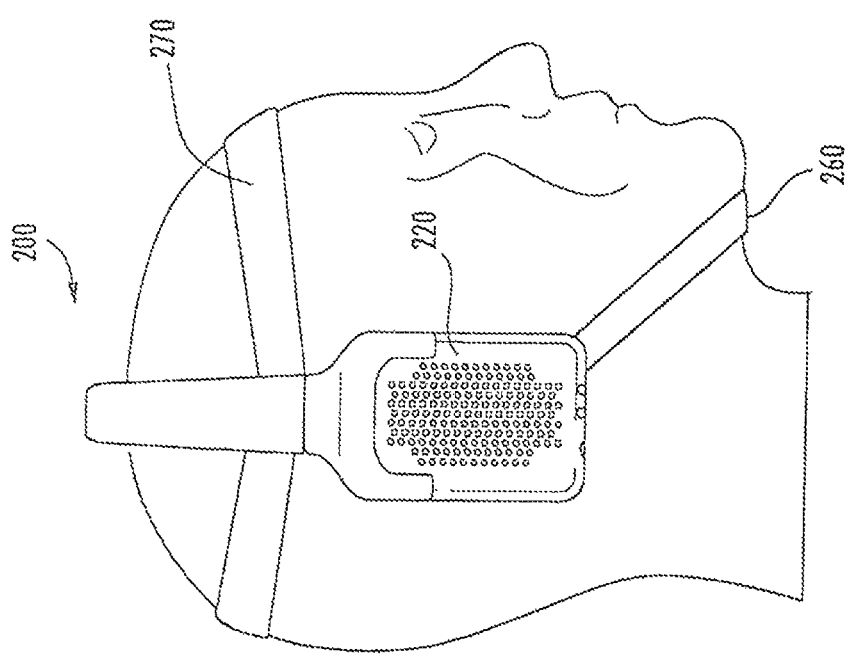
FIG. 3

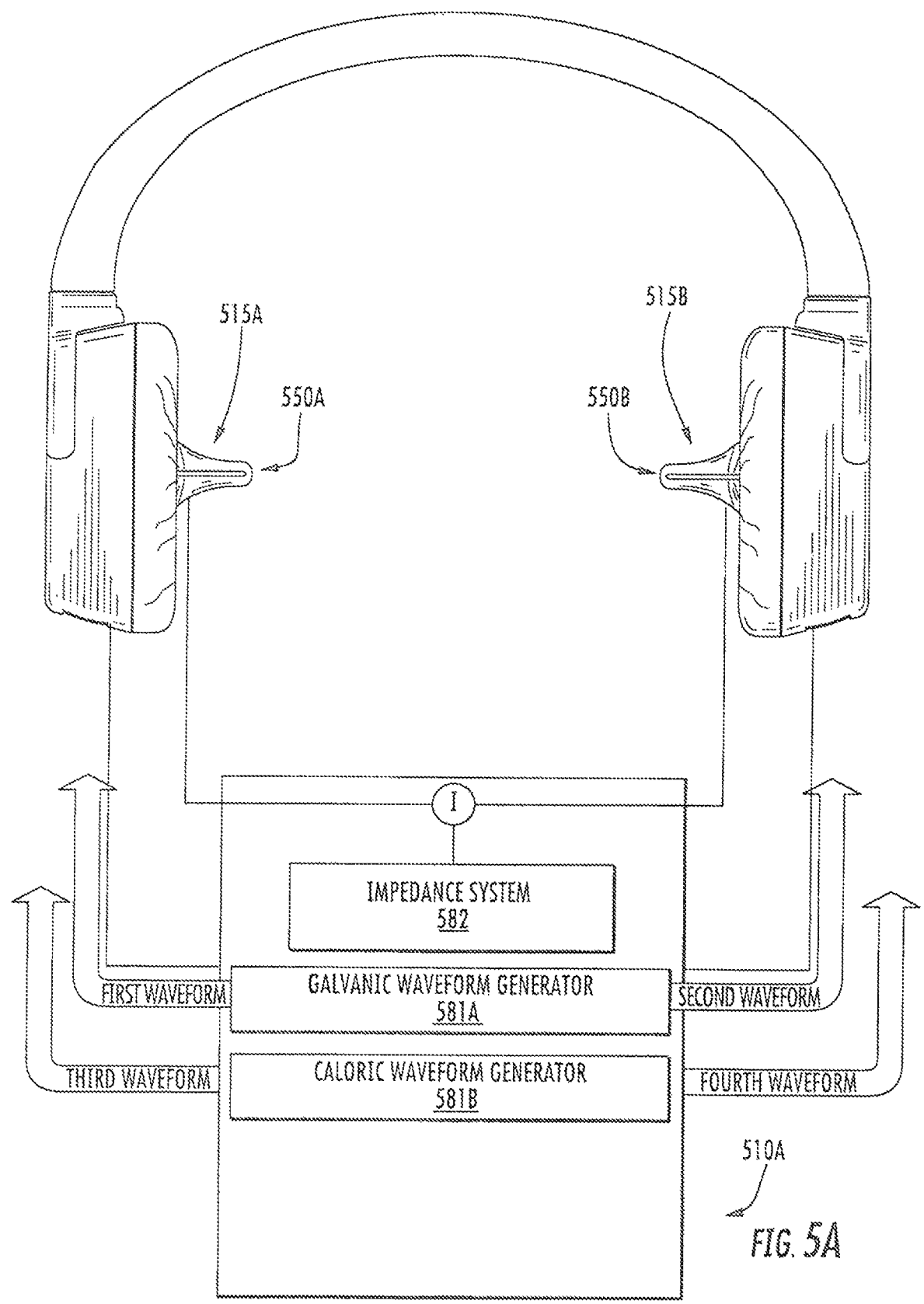

SYSTEMS, DEVICES AND METHODS INCLUDING GALVANIC AND CALORIC VESTIBULAR STIMULATION

CROSS-REFERENCE TO RELATED APPLICATIONS

This application is a continuation of U.S. patent application Ser. No. 15/914,516, filed on Mar. 7, 2018, which is a continuation-in-part of PCT Application No PCT/US2016/049824, filed Sep. 1, 2016, which in turn claims priority to U.S. Provisional Patent Application No. 62/214,474, filed Sep. 4, 2015, and U.S. Provisional Patent Application No. 62/322,985, filed Apr. 15, 2016, the entire contents of each of which is incorporated herein by reference. U.S. patent application Ser. No. 15/914,516, filed on Mar. 7, 2018, is also a continuation-in-part of PCT Application No PCT/US2016/049827, filed Sep. 1, 2016, which in turn claims priority to U.S. Provisional Patent Application No. 62/214,474, filed Sep. 4, 2015, and U.S. Provisional Patent Application No. 62/322,985, filed Apr. 15, 2016, the entire contents of each of which is incorporated herein by reference. U.S. patent application Ser. No. 15/914,516, filed on Mar. 7, 2018, is also a continuation-in-part of PCT Application No PCT/US2016/049836, filed Sep. 1, 2016, which in turn claims priority to U.S. Provisional Patent Application No. 62/214,474, filed Sep. 4, 2015, and U.S. Provisional Patent Application No. 62/322,985, filed Apr. 15, 2016, the entire contents of each of which is incorporated herein by reference.

FIELD OF THE INVENTION

The present invention relates to neurostimulation, and in particular, to neurostimulation systems, devices, and methods.

BACKGROUND

Neurostimulation is the therapeutic and/or diagnostic activation of one or more parts of the nervous system. The nervous system may be electrically stimulated through invasive means, such as implantable electrodes, or though less invasive means, such as electrodes attached to the skin. Non-electrical forms of neurostimulation may employ electromagnetic waves, light, sound, or temperature to stimulate the nervous system. Neurostimulation has been used for the purpose of medical treatment and/or diagnosis of various disorders.

Vestibular stimulation is a form of neurostimulation that stimulates the vestibular branch of the vestibulocochlear nerve, the eighth cranial nerve. As used herein, "vestibular nerve" shall refer to the vestibular branch of the eighth cranial nerve. The vestibular nerve may be stimulated electrically, termed Galvanic Vestibular Stimulation ("GVS"), or may be stimulated using temperature, termed Caloric Vestibular Stimulation.

Some conventional two-pole GVS systems provide an electrical current between the left and right mastoid bones, adjacent to the mastoid processes, to pass through the vestibular organs in the inner ear. Some conventional three-pole GVS systems provide electrical currents between the forehead and the left and right mastoids. In order to overcome the electrical impedance of the skin, the skin may be abraded, a conductive gel may be used, and/or a higher voltage may be used to provide the desired electrical current. See, e.g., R. C. Fitzpatrick, B. L. Day, Probing the human vestibular system with galvanic stimulation. *J Appl Physiol* 96, 2301-2316 (2004); published online EpubJun (10.1152/japplphysiol.00008.2004).

Accordingly, apparatuses and associated methods useful for delivering lower voltage stimulation to the nervous system and/or the vestibular system of an individual are potentially beneficial to take full advantage of physiological responses that are useful in diagnosing and/or treating a variety of medical conditions.

SUMMARY OF EMBODIMENTS OF THE INVENTION

According to some embodiments, methods of neurostimulation are provided. A method of neurostimulation may include delivering a modulated electrical signal to a patient through galvanic vestibular stimulation (GVS) and delivering a time varying thermal waveform to the patient through caloric vestibular stimulation (CVS) simultaneous with the delivery of the modulated electrical signal through GVS.

In some embodiments, the time varying thermal waveform may be delivered via an earpiece that is configured to be inserted in an ear of the patient. The earpiece may include an electrode. The modulated electrical signal may be delivered via the electrode.

In some embodiments, the modulated electrical signal may be configured to excite different frequencies than the time varying thermal waveform.

In some embodiments, the modulated electrical signal may be configured to excite frequencies greater than 1 Hz and the time varying thermal waveform may be configured to excite frequencies less than 1 Hz.

In some embodiments, the modulated electrical signal may be configured to excite frequencies that are at least 10 times greater than a maximum of frequencies that the time varying thermal waveform is configured to excite.

In some embodiments, the method may include controlling the modulated electrical signal and the time varying thermal waveform to maintain a defined phase difference between the modulated electrical signal and the time varying thermal waveform.

In some embodiments, the method may include controlling the modulated electrical signal to be approximately 180° out of phase with the time varying thermal waveform.

In some embodiments, the method may include producing a net stimulation at a beat frequency equal to a difference between a frequency of the modulated electrical signal and a frequency of the time varying thermal waveform by controlling the frequency of the modulated electrical signal relative to the frequency of the time varying thermal waveform.

In some embodiments, the CVS and/or GVS may be configured to increase a passage of IGF-1 through a blood-brain-barrier.

In some embodiments, the CVS may be configured to produce oscillations in a cerebral blood flow.

In some embodiments, the time varying thermal waveform may be configured to facilitate the production of the oscillations in the cerebral blood flow.

In some embodiments, the method may include sequentially applying a plurality of time varying thermal waveforms, measuring respective cerebral blood flow oscillations resulting from the plurality of time varying thermal waveforms, and selecting at least one of the plurality of time varying thermal waveforms that produces an effective amplitude of cerebral blood flow oscillations. The delivering the time varying thermal waveform to the patient through CVS simultaneous with the delivery of the modulated electrical signal through GVS may include delivering the selected at least one of the plurality of time varying thermal waveforms.

In some embodiments, the modulated electrical signal may be configured to activate a subset of brain regions for the increase in passage of IGF-1 through the blood-brain-barrier.

In some embodiments, the method may include introducing a positron-emitting radionuclide and using Positron Emission Tomography (PET) scanning to detect the increase in passage of IGF-1 through the blood-brain-barrier.

In some embodiments, the positron-emitting radionuclide may be a PET label on IGF-1.

In some embodiments, the positron-emitting radionuclide may be a PET label on glucose.

In some embodiments, the positron-emitting radionuclide may be a PET label on oxygen.

In some embodiments, the modulated electrical signal and/or the time varying thermal waveform may be configured to reduce symptoms of a neurological disease.

In some embodiments, the modulated electrical signal and/or the time varying thermal waveform may be configured to reduce symptoms of Parkinson's disease.

In some embodiments, the modulated electrical signal and/or the time varying thermal waveform may be configured to reduce symptoms of migraine headache.

According to some embodiments, neurostimulation devices are provided. A neurostimulation device may include first and second electrodes, first and second thermoelectric devices thermally coupled, respectively, to first and second earpieces configured to be insertable into respective ear canals of a patient, and a controller including a waveform generator. The controller may be configured to deliver a modulated electric signal to the patient through galvanic vestibular stimulation (GVS) using the first and second electrodes and to deliver a time varying thermal waveform to the patient through caloric vestibular stimulation (CVS) using the first and second earpieces simultaneous with the delivery of the modulated electrical signal through GVS.

In some embodiments, the first and second earpieces may include the first and second electrodes, respectively.

In some embodiments, the modulated electrical signal may be configured to excite different frequencies than the time varying thermal waveform.

In some embodiments, the modulated electrical signal may be configured to excite frequencies greater than 1 Hz and the time varying thermal waveform may be configured to excite frequencies less than 1 Hz.

In some embodiments, the modulated electrical signal may be configured to excite frequencies that are at least 10 times greater than a maximum of frequencies that the time varying thermal waveform is configured to excite.

In some embodiments, the controller may be configured to control the modulated electrical signal and the time varying thermal waveform to maintain a defined phase difference between the modulated electrical signal and the time varying thermal waveform.

In some embodiments, the controller may be configured to control the modulated electrical signal to be approximately 180° out of phase with the time varying thermal waveform.

In some embodiments, the controller may be configured to producing a net stimulation at a beat frequency equal to a difference between a frequency of the modulated electrical signal and a frequency of the time varying thermal waveform by controlling the frequency of the modulated electrical signal relative to the frequency of the time varying thermal waveform.

In some embodiments, the CVS and/or GVS may be configured to increase a passage of IGF-1 through a blood-brain-barrier.

In some embodiments, the CVS may be configured to produce oscillations in a cerebral blood flow.

In some embodiments, the time varying thermal waveform may be configured to facilitate the production of the oscillations in the cerebral blood flow.

In some embodiments, the controller may be configured to sequentially apply a plurality of time varying thermal waveforms, measure respective cerebral blood flow oscillations resulting from the plurality of time varying thermal waveforms, and select at least one of the plurality of time varying thermal waveforms that produces an effective amplitude of cerebral blood flow oscillations. The controller may be configured to deliver the time varying thermal waveform to the patient through CVS simultaneous with the delivery of the modulated electrical signal through GVS by delivering the selected at least one of the plurality of time varying thermal waveforms.

In some embodiments, the modulated electrical signal may be configured to activate a subset of brain regions for the increase in passage of IGF-1 through the blood-brain-barrier.

In some embodiments, the modulated electrical signal and/or the time varying thermal waveform may be configured to reduce symptoms of a neurological disease.

In some embodiments, the modulated electrical signal and/or the time varying thermal waveform may be configured to reduce symptoms of Parkinson's disease.

In some embodiments, the modulated electrical signal and/or the time varying thermal waveform may be configured to reduce symptoms of migraine headache.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 3 is a front and side view illustrating a user wearing a stimulation device according to some embodiments of the present invention;

FIGS. 5A and 5B are schematic block diagrams illustrating stimulation devices according to some embodiments of the present invention;

DETAILED DESCRIPTION OF EMBODIMENTS OF THE INVENTION

Figure 1:
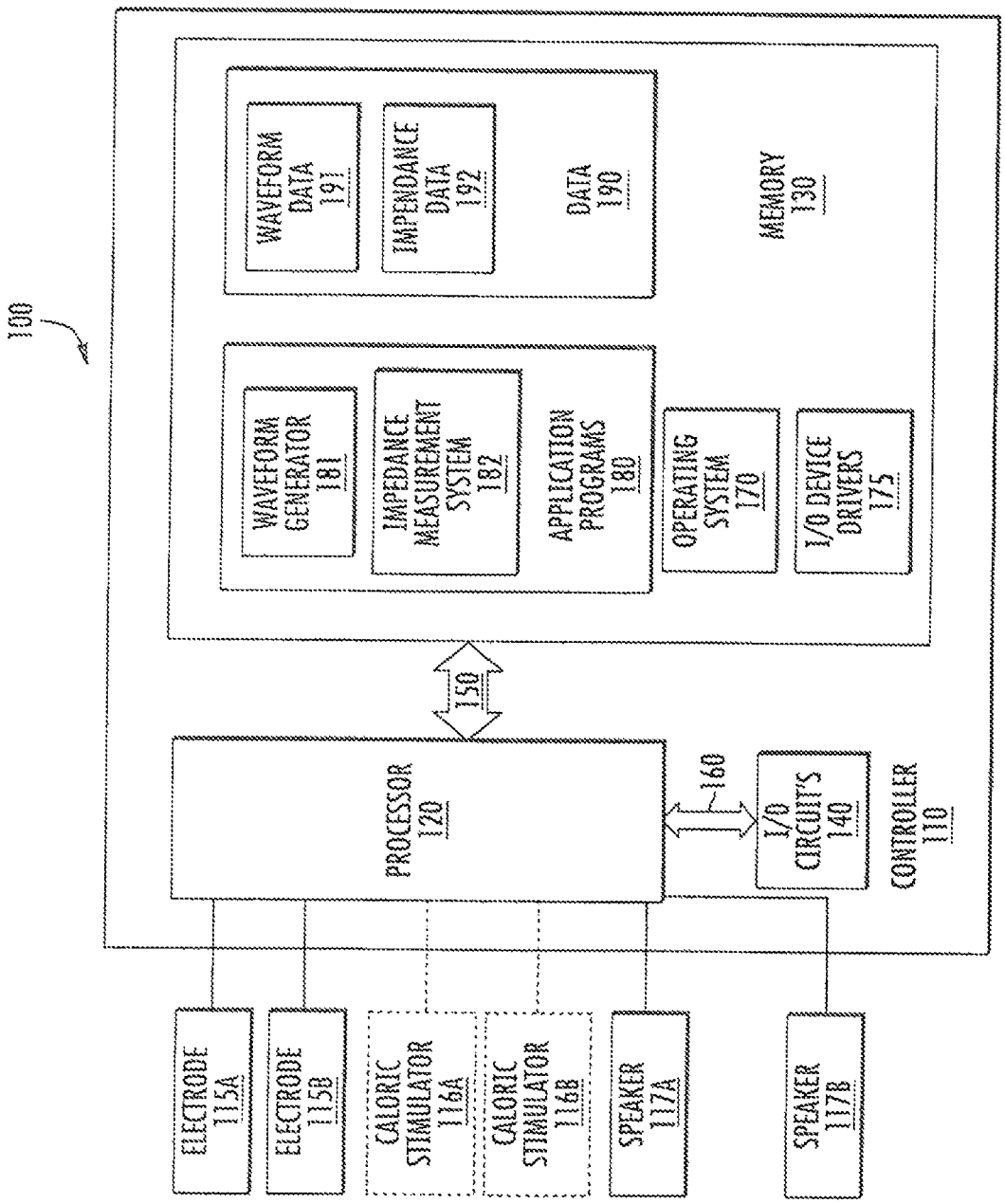
FIG. 1 is a schematic block diagram illustrating stimulation devices, methods, and systems according to some embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

Definitions

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that one or more blocks of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory such as an SD card), an optical fiber, and a portable compact disc read-only memory (CD-ROM).

As used herein, the term "vestibular system" has the meaning ascribed to it in the medical arts and includes but is not limited to those portions of the inner ear known as the vestibular apparatus and the vestibulocochlear nerve. The vestibular system, therefore, further includes, but is not limited to, those parts of the brain that process signals from the vestibulocochlear nerve.

"Treatment," "treat," and "treating" refer to reversing, alleviating, reducing the severity of, delaying the onset of, inhibiting the progress of, or preventing a disease or disorder as described herein, or at least one symptom of a disease or disorder as described herein (e.g., treating one or more of tremors, bradykinesia, rigidity or postural instability associated with Parkinson's disease; treating one or more of intrusive symptoms (e.g., dissociative states, flashbacks, intrusive emotions, intrusive memories, nightmares, and night terrors), avoidant symptoms (e.g., avoiding emotions, avoiding relationships, avoiding responsibility for others, avoiding situations reminiscent of the traumatic event), hyperarousal symptoms (e.g., exaggerated startle reaction, explosive outbursts, extreme vigilance, irritability, panic symptoms, sleep disturbance) associated with post-traumatic stress disorder). In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence. Treatment may comprise providing neuroprotection, enhancing cognition and/or increasing cognitive reserve. Treatment may be as an adjuvant treatment as further described herein.

"Adjuvant treatment" as described herein refers to a treatment session in which the delivery of one or more galvanic and/or caloric waveforms to the vestibular system and/or the nervous system of a patient modifies the effect(s) of one or more active agents and/or therapies. For example, the delivery of one or more thermal waveforms to the vestibular system and/or the nervous system of a patient may enhance the effectiveness of a pharmaceutical agent (by restoring the therapeutic efficacy of a drug to which the patient had previously become habituated, for example). Likewise, the delivery of one or more galvanic and/or caloric waveforms to the vestibular system and/or the nervous system of a patient may enhance the effectiveness of counseling or psychotherapy. In some embodiments, delivery of one or more galvanic and/or caloric waveforms to the vestibular system and/or the nervous system of a patient may reduce or eliminate the need for one or more active agents and/or therapies. Adjuvant treatments may be effectuated by delivering one or more galvanic and/or caloric waveforms to the vestibular system and/or the nervous system of a patient prior to, currently with and/or after administration of one or more active agents and/or therapies.

"Chronic treatment," "Chronically treating," or the like refers to a therapeutic treatment carried out at least 2 to 3 times a week (or in some embodiments at least daily) over an extended period of time (typically at least one to two weeks, and in some embodiments at least one to two months), for as long as required to achieve and/or maintain therapeutic efficacy for the particular condition or disorder for which the treatment is carried out.

"Waveform" or "waveform stimulus" as used herein refers to the galvanic and/or caloric stimulus delivered to a subject through a suitable apparatus to carry out the methods described herein. "Waveform" is not to be confused with "frequency," the latter term concerning the rate of delivery of a particular waveform. The term "waveform" is used herein to refer to one complete cycle thereof, unless additional cycles (of the same, or different, waveform) are indicated. As discussed further below, time-varying waveforms may be preferred over constant applications in carrying out the present invention.

"Actively controlled waveform" or "actively controlled time-varying waveform" as used herein refers to a waveform stimulus in which the intensity of the stimulus is repeatedly adjusted, or substantially continuously adjusted or driven, throughout the treatment session, typically by control circuitry or a controller in response to active feedback from a suitably situated sensor, so that drift of the stimulus from that which is intended for delivery which would otherwise occur due to patient contact is minimized.

"Packets of electrical pulses" as used herein refers to a series of at least two electrical pulses, wherein the pulses are separated apart from each other in time by a first time period and the last pulse of one packet is separated apart from the first pulse of the next packet by a second time period, the second time period being greater than the first time period. Although the electrical pulses are illustrated herein as a square wave, some embodiments of the inventive concept may include sinusoidal, sawtooth, or other suitable waveforms.

"Modulation," "modulated signal," or "modulated waveform" as used herein refers to varying one or more parameters of a signal or waveform over time. For example, in a modulated waveform comprising a plurality of packets of electrical pulses, one or more parameters may vary from one packet to another.

Subjects may be treated with the present invention for any reason. In some embodiments, disorders for which treatment may be carried out include, include, but are not limited to, migraine headaches (acute and chronic), depression, anxiety (e.g. as experienced in post-traumatic stress disorder ("PTSD") or other anxiety disorders), spatial neglect, Parkinson's disease, seizures (e.g., epileptic seizures), diabetes (e.g., type II diabetes), etc.

Headaches that may be treated by the methods and apparatuses of the present invention include, but are not limited to, primary headaches (e.g., migraine headaches, tension-type headaches, trigeminal autonomic cephalalgias and other primary headaches, such as cough headaches and exertional headaches) and secondary headaches. See, e.g., International Headache Society Classification ICHD-II.

Migraine headaches that may be treated by the methods and apparatuses of the present invention may be acute/chronic and unilateral/bilateral. The migraine headache may be of any type, including, but not limited to, migraine with aura, migraine without aura, hemiplegic migraine, ophthalmoplegic migraine, retinal migraine, basilar artery migraine, abdominal migraine, vestibular migraine and probable migraine. As used herein, the term "vestibular migraine" refers to migraine with associated vestibular symptoms, including, but not limited to, head motion intolerance, unsteadiness, dizziness and vertigo. Vestibular migraine includes, but is not limited to, those conditions sometimes referred to as vertigo with migraine, migraine-associated dizziness, migraine-related vestibulopathy, migrainous vertigo and migraine-related vertigo. See, e.g., Teggi et al., HEADACHE 49:435-444 (2009).

Tension-type headaches that may be treated by the methods and apparatuses of the present invention, include, but are not limited to, infrequent episodic tension-type headaches, frequent episodic tension-type headaches, chronic tension-type headache and probable tension-type headache.

Trigeminal autonomic cephalalgias that may be treated by the methods and apparatuses of the present invention, include, but are not limited to, cluster headaches, paroxysmal hemicranias, short-lasting unilateral neuralgiform headache attacks with conjunctival injection and tearing and probable trigeminal autonomic cephalalgias. Cluster headache, sometimes referred to as "suicide headache," is considered different from migraine headache. Cluster headache is a neurological disease that involves, as its most prominent feature, an immense degree of pain. "Cluster" refers to the tendency of these headaches to occur periodically, with active periods interrupted by spontaneous remissions. The cause of the disease is currently unknown. Cluster headaches affect approximately 0.1% of the population, and men are more commonly affected than women (in contrast to migraine headache, where women are more commonly affected than men).

Other primary headaches that may be treated by the methods and apparatuses of the present invention, include, but are not limited to, primary cough headache, primary exertional headache, primary headache associated with sexual activity, hypnic headache, primary thunderclap headache, hemicranias continua and new daily-persistent headache.

Additional disorders and conditions that can be treated by the methods and systems of the present invention include, but are not limited to, neuropathic pain (e.g., migraine headaches), tinnitus, brain injury (acute brain injury, excitotoxic brain injury, traumatic brain injury, etc.), spinal cord injury, body image or integrity disorders (e.g., spatial neglect), visual intrusive imagery, neuropsychiatric disorders (e.g. depression), bipolar disorder, neurodegenerative disorders (e.g. Parkinson's disease), asthma, dementia, insomnia, stroke, cellular ischemia, metabolic disorders, (e.g., diabetes), post-traumatic stress disorder ("PTSD"), addictive disorders, sensory disorders, motor disorders, and cognitive disorders.

Sensory disorders that may be treated by the methods and apparatuses of the present invention include, but are not limited to, vertigo, dizziness, seasickness, travel sickness cybersickness, sensory processing disorder, hyperacusis, fibromyalgia, neuropathic pain (including, but not limited to, complex regional pain syndrome, phantom limb pain, thalamic pain syndrome, craniofacial pain, cranial neuropathy, autonomic neuropathy, and peripheral neuropathy (including, but not limited to, entrapment-, heredity-, acute inflammatory-, diabetes-, alcoholism-, industrial toxin-, Leprosy-, Epstein Barr Virus-, liver disease-, ischemia-, and drug-induced neuropathy)), numbness, hemianesthesia, and nerve/root plexus disorders (including, but not limited to, traumatic radiculopathies, neoplastic radiculopathies, vasculitis, and radiation plexopathy).

Motor disorders that may be treated by the method and apparatuses of the present invention include, but are not limited to, upper motor neuron disorders such as spastic paraplegia, lower motor neuron disorders such as spinal muscular atrophy and bulbar palsy, combined upper and lower motor neuron syndromes such as familial amyotrophic lateral sclerosis and primary lateral sclerosis, and movement disorders (including, but not limited to, Parkinson's disease, tremor, dystonia, Tourette Syndrome, myoclonus, chorea, nystagmus, spasticity, agraphia, dysgraphia, alien limb syndrome, and drug-induced movement disorders).

Cognitive disorders that may be treated by the method and apparatuses of the present invention include, but are not limited to, schizophrenia, addiction, anxiety disorders, depression, bipolar disorder, dementia, insomnia, narcolepsy, autism, Alzheimer's disease, anomia, aphasia, dysphasia, parosmia, spatial neglect, attention deficit hyperactivity disorder, obsessive compulsive disorder, eating disorders, body image disorders, body integrity disorders, post-traumatic stress disorder, intrusive imagery disorders, and mutism.

Metabolic disorders that may be treated by the present invention include diabetes (particularly type II diabetes), hypertension, obesity, etc.

Addiction, addictive disorders, or addictive behavior that may be treated by the present invention includes, but is not limited to, alcohol addiction, tobacco or nicotine addiction (e.g., using the present invention as a smoking cessation aid), drug addictions (e.g., opiates, oxycontin, amphetamines, etc.), food addictions (compulsive eating disorders), etc.

In some embodiments, the subject has two or more of the above conditions, and both conditions are treated concurrently with the methods and systems of the invention. For example, a subject with both depression and anxiety (e.g., PTSD) can be treated for both, concurrently, with the methods and systems of the present invention.

The methods and systems according to embodiments of the present invention utilize galvanic and/or caloric stimulation to induce physiological and/or psychological responses in a subject for medically diagnostic and/or therapeutic purposes. Subjects to be treated and/or stimulated with the methods, devices and systems of the present invention include both human subjects and animal subjects. In particular, embodiments of the present invention may be used to diagnose and/or treat mammalian subjects such as cats, dogs, monkeys, etc. for medical research or veterinary purposes.

As noted above, some embodiments according to the present invention utilize galvanic and/or caloric stimulation to administer stimulation in the ear canal of the subject. The ear canal serves as a useful conduit to the individual's vestibular system and to the vestibulocochlear nerve. Without wishing to be bound by any particular theory, it is believed that galvanic and/or caloric stimulation of the vestibular system is translated into electrical stimulation within the central nervous system ("CNS") and propagated throughout the brain, including but not limited to the brain stem, resulting in certain physiological changes that may be useful in treating various disease states (increased blood flow, generation of neurotransmitters, etc). See, e.g., Zhang, et al. *Chinese Medical J.* 121:12:1120 (2008) (demonstrating increased ascorbic acid concentration in response to cold water CVS).

Some embodiments according to the present invention utilize the galvanic and/or caloric stimulation to entrain brain waves at a target frequency and/or within a target portion of the brain. Brainwave entrainment is any practice that aims to cause brainwave frequencies to fall into step with a periodic stimulus having a frequency corresponding to an intended brain-state or having a different frequency that induces entrainment by cross frequency coupling. Without wishing to be bound by any particular theory, it is believed that when the brain is presented with a rhythmic stimulus, the rhythm is reproduced in the brain in the form of electrical impulses. If the rhythm resembles the natural internal rhythms of the brain, brainwaves, the brain may respond by synchronizing its own electric cycles to the same rhythm. Examples of entrainment descriptors include: phase amplitude coupling, cross frequency coupling, and amplitude-amplitude coupling. The entrained brain waves may continue at the entrained frequency for some time after the stimulus is removed.

Without wishing to be bound by any particular theory, it is currently believed that various brain waves may be entrained by stimulation. For example, different subcortical structures may be associated with different frequencies of brain wave modulations. See, e.g., K Omata, T Hanakawa, M Morimoto, M Honda, Spontaneous Slow Fluctuation of EEG Alpha Rhythm Reflects Activity in Deep-Brain Structures: A Simultaneous EEG-fMRT Study. *PLoS ONE*, vol 8, issue 6, e66869 (June 2013). Therefore, according to some embodiments of the present invention, stimulation frequencies and/or modulation frequencies may be selected corresponding to a region of the brain for which activation is desired. For example, the selected frequencies may correspond to the frequencies naturally associated with a region of the brain. Brain waves may be measured using electroencephalogram (EEG). The realization that time-varying signals could be picked up on the scalp preceded any detailed understanding of what was being recorded. EEG signal results from the collective action of a region of neurons that fire synchronously. That a voltage can be detected at all at the scalp is a result of the finite length over which voltage differences develop in the cortex (and EEG can only pick up signals from the cortex). Intraoperatively, there is a method called ECoG (electrocorticography) wherein an electrode array is placed directly on the surface of the cortex. This allows for finer scale measurements, but may be limited to patients undergoing brain surgery. ECoG generally confirms the findings of EEG in terms of larger-area synchronous firing. Historically, EEG signals were divided into non-overlapping frequency bands such that researchers had a common reference point for brain activity. This approach provided a gross map of important brain rhythms. For instance, the alpha band (8-13 Hz) may change a lot (increases power) when the eyes are closed and one focuses on internal thinking versus sensory perception. The gamma band (30-100+Hz) may be associated with global "binding" and may be a marker of unitary thought processes. Brain waves in several bands may be entrained, for example, by listening to music. See, e.g., Doelling, K. B., & Poeppel, D., Cortical entrainment to music and its modulation by expertise. Proceedings of the National Academy of Sciences, vol 112, no. 45, E6233-E6242 (Nov. 10, 2015).

Modulation of brain waves may be used for therapeutic effects. For example, non-invasive brain stimulation (NIBS) may improve behavioral performance in patients that have had a stroke or are suffering from neuropsychiatric disorders, such as Parkinson's disease (PD) or schizophrenia (SCZ). See, e.g., Krawinkel L K, Engel A K, & Hummel F C, Modulating pathological oscillations by rhythmic non-invasive brain stimulation—a therapeutic concept?, first published online at http://biorxiv.org/content/early/2015/01/29/014548 (Jan. 29, 2015), also published in Front. Syst. Neurosci. (Mar. 17, 2015). Some disorders, such as PD may be associated with significant alterations in connectivity between brain regions. See, e.g., Tropini G, Chiang J, Wang Z J, Ty E, & McKeown M J, Altered directional connectivity in Parkinson's disease during performance of a visually guided task, NeuroImage, vol. 56, issue 4, 2144-2156 (Jun. 15, 2011). PD patients have been found to have significantly lower interhemispheric EEG coherence in various frequencies than healthy control subjects, which may impair an ability of the PD patients cognitive and emotional functioning. See, e.g., Yuvaraj R, Murugappan M, Ibrahim N M, Sundaraj K, Omar M I, Mohamad K, Palaniappan R, & Satiyan M, Inter-hemispheric EEG coherence analysis in Parkinson's disease: Assessing brain activity during emotion processing, J Neural Transm, 122:237-252 (2015). Some of the effects of PD may be improved by the therapeutic use of neurostimulation. See, e.g., Kim D J, Yogendrakumar V, Chiang J, Ty E, Wang Z J, & McKeown M J, Noisy Galvanic Vestibular Stimulation Modulates the Amplitude of EEG Synchrony Patterns, PLoS ONE, vol. 8, issue 7, e69055 (July 2013). Therapeutic neurostimulation may decouple inter-frequency activity to reduce or reverse abnormalities found in patients with neuropsychiatric disorders, such as PD. See, e.g., de Hemptinne C, Swann N C, Ostrem J L, Ryapolova-Webb E S, San Luciano M, Galifianakis N B, & Starr P A, Therapeutic deep brain stimulation reduces cortical phase-amplitude coupling in Parkinson's disease, Nature Neuroscience, vol. 8, 779-786 (2015).

Aberrant EEG activity has been documented in patients with some neuropsychiatric disorders, such as PD. Noninvasive neuromodulation may be used to alter EEG. This can take the form of disrupting the dysfunctional rhythm or trying to entrain and thus guide the aberrant rhythm to a "proper" state. Success in achieving neuromodulation may be assessed by, for example, re-measuring EEG activity to see if the abnormal power levels and/or abnormal cross-frequency coupling has been addressed. Therefore, according to some embodiments, a therapeutic method may include identifying an EEG abnormality and prescribing an associated therapeutic rhythm. The method may include choosing a frequency range/ranges for neurostimulation, such as with GVS, that may couple to the abnormal oscillations. The chosen frequency range/ranges may not be exactly the same as frequencies of the EEG abnormality because cross-frequency coupling can occur. The method may include administering the "corrective" GVS stimulation repeatedly over time. For example, the administration may continue until the desired change may be measured. The desired change may be measured, for example, using EEG or may be measured using other methods. In some embodiments, the effects may be measured by measuring a heart rate variability (HRV).

Some embodiments according to the present invention utilize a combination of galvanic and caloric stimulation. In such embodiments, the galvanic vestibular stimulation may enhance a delivery of the caloric vestibular stimulation.

As noted above, some embodiments according to the present invention utilize galvanic stimulation to administer stimulation in the ear canal of the subject. A modulated electrical signal may be transmitted through the skin lining the ear canal to stimulate the vestibular system of the subject. The skin may provide an electrical resistance in the electrical path between the electrode and the vestibular system. The electrical resistance of the skin may be generally inversely proportional to the frequency of the electrical signal. Thus, in order to stimulate the vestibular system at lower frequencies, a waveform of larger amplitude may be required than a waveform at higher frequencies. The larger amplitude may not be desired as the subject may experience discomfort, pain, and/or physical damage based on the large voltage. However, the higher frequencies may not induce the desired diagnostic and/or therapeutic effects of galvanic vestibular stimulation. For example, some diagnostic and/or therapeutic uses of galvanic vestibular stimulation desire stimulation at lower frequencies. See, e.g., G. C. Albert, C. M. Cook, F. S. Prato, A. W. Thomas, Deep brain stimulation, vagal nerve stimulation and transcranial stimulation: An overview of stimulation parameters and neurotransmitter release. *Neurosci Biobehav Rev* 33, 1042-1060 (2009); published online EpubJul (10.1016/j.neubiorev.2009.04.006) (reviewing parameters of stimulation techniques that explore or treat neurological disorders). In some embodiments of the present invention, a modulation scheme is provided that generates an electrical signal with a higher frequency to produce the lower impedance and that stimulates the vestibular system at a lower frequency.

For example, the modulation scheme may provide a repeating series of spaced-apart packets of electronic pulses. The electronic pulses within the packets may be closely separated in time to provide the higher frequency and, thus, to produce the lower impedance that permits transmission through the skin. One or more parameters may be modulated according to a lower frequency. For example, one or more of the quantity of the plurality of pulses within ones of the plurality of packets of pulses, the width in time of the plurality of electrical pulses within ones of the plurality of packets of pulses, the amplitude of the plurality of pulses within ones of the plurality of packets of pulses, the separation in time between adjacent ones of the plurality of pulses within ones of the plurality of packets of pulses, and the separation in time between adjacent ones of the plurality of packets of pulses may be modulated. The vestibular system may be stimulated based on the lower frequency. For example, the lower frequency modulation may entrain brainwaves based on the low frequency of the modulation. Thus, the modulation scheme may produce the lower impedance based on the higher frequency of the pulses within a packet and stimulate the vestibular system based on the lower frequency of the modulation.

In other embodiments, the modulation scheme may provide an electrical signal. The electrical signal may include a carrier function that includes an amplitude and a carrier frequency. For example, the carrier function may be a sine wave. However, in other embodiments the function may be another function such as a square wave, sawtooth wave, or another function. The frequency of the carrier function may be sufficiently high to produce the lower impedance that permits transmission through the skin. One or more parameters of the carrier function may be modulated according to modulation waveform. For example, one or more of the amplitude and frequency of the carrier function may be modulated to produce a modulated electrical signal. A frequency of the modulation waveform may be lower than the frequency of the carrier function. The vestibular system may be stimulated based on the lower frequency. For example, the lower frequency modulation may entrain brainwaves based on the low frequency of the modulation. Thus, the modulation scheme may produce the lower impedance based on the higher frequency of the pulses within a packet and stimulate the vestibular system based on the lower frequency of the modulation.

Some embodiments according to the present invention utilize sound-based stimulation and/or electronic stimulation based on sounds. Sounds may affect brain activity. For example, sounds containing significant quantities of non-stationary high-frequency components (HFCs) above the human audible range (approximately 20 kHz) may activate the midbrain and diencephalon and evoke various physiological, psychological and behavioral responses. See, e.g., Fukushima A, Yagi R, Kawai N, Honda M, Nishina E, & Oohashi T, Frequencies of Inaudible High-Frequency Sounds Differentially Affect Brain Activity: Positive and Negative Hypersonic Effects, PLoS ONE, vol. 9, issue 4, e95464 (April 2014). Sounds have been shown to activate vestibular responses at least up to 2000 Hz. See, e.g., Welgampola M S, Rosengren S M, Halmagyi G M, & Colebatch J G, Vestibular activation by bone conducted sound, J Neurol Neurosurg Psychiatry, 74:771-778 (2003). Without wishing to be bound by any particular theory, it is believed that the vestibular response to sound may be a leftover trait from early evolution when the vestibular system was the organ of sound detection when animals lived in the water. The cochlea developed after animals lived on land and enabled better hearing in the air environment. Since the basic hair cell configuration is similar in the cochlea and vestibular organs, the basic ability to respond to a range of frequencies may be very similar, if not identical. Since hearing can occur up to approximately 20 KHz in humans, the vestibular system may also respond likewise. Above approximately 1 kHz, an A. C. component of cochlear response may be dominated by a D. C. response. See, e.g., A. R. Palmer and I. J. Russell, Phase-locking in the cochlear nerve of the guinea-pig and its relation to the receptor potential of inner hair-cells, Hearing research, vol. 24, 1-15 at FIG. 9 (1986). Therefore, even at the 2000 Hz that has been shown to provide vestibular response, the nerve may not be able to follow the stimulus sound wave and instead a direct current, DC, offset may occur.

System

FIG. 1 is a schematic block diagram illustrating a stimulation device according to some embodiments of the present invention. Referring to FIG. 1, a stimulation device 100 may include a controller 110 coupled to electrodes 115A, 115B. In some embodiments, the controller 110 may optionally be also coupled to caloric stimulators 116A, 116B. In some embodiments, the controller 110 may optionally be also coupled to speakers 117A, 117B. The controller 110 may include a processor 120, I/O circuits 140, and/or memory 130. The memory may include an operating system 170, I/O device drivers 175, applications programs 180, and/or data 190. The application programs 180 may include a waveform generator 181 and/or a measurement system 182. The data 190 may include waveform data 191 and/or measurement data 192. Although illustrated as software, one or more functions of the application programs 180 may be implemented in hardware or in any combination of hardware and/or software. Additionally, it should be understood that one or more functions of the functions of the stimulation device 100 may be provided by one or more separate devices. For example, one or more portions of the data 190 may be stored remote from the stimulation device 100.

According to some embodiments of the present invention, the stimulation device 100 may stimulate a nervous system by providing first and second waveforms to a first electrode 115A and a second electrode 115B. In some embodiments, the first and second waveforms may be modulated electric signals. In some embodiments, the first and second waveforms may be a modulated voltage level between the electrodes 115A, 115B. In some embodiments, the first and second waveforms may be a modulated electrical current between the electrodes 115A, 115B. For example, the first and second waveforms may be asymmetric with respect to each other to provide the modulated voltage level and/or modulated electrical current between the electrodes 115A, 115B. Other embodiments may include one or more neutral connections to the subject. For example, in some embodiments, the first waveform may be a modulated voltage level between the first electrode 115A and at least one of the neutral connections and the second waveform may be a modulated voltage level between the second electrode 115B and at least one of the neutral connections. In some embodiments, the first waveform may be a modulated electrical current between the first electrode 115A and at least one of the neutral connections and the second waveform may be a modulated electrical current between the second electrode 115B and at least one of the neutral connections. Thus the electrodes 115A, 115B may be used together to provide one stimulus or may be used independently to provide more than one stimulus.

The controller 110 may generate the first and second waveforms. The controller 110 may include the memory 130, the processor 120 and the I/O circuits 140 and may be operatively and communicatively coupled to the electrodes 115A, 115B. The processor 120 may communicate with the memory 130 via an address/data bus 150 and with the I/O circuits 140 via an address/data bus 160. As will be appreciated by one of skill in the art, the processor 120 may be any commercially available or custom microprocessor. The memory 130 may be representative of the overall hierarchy of memory devices containing software and data used to implement the functionality of the stimulation device 100. Memory 130 may include, but is not limited to, the following types of devices: cache, ROM, PROM, EPROM, EEPROM, flash memory, SRAM and DRAM. Memory 130 may include non-volatile memory.

As shown in FIG. 1, the memory 130 may comprise several categories of software and data. For example, the memory may include one or more of: the operating system 170, applications 180, data 190, and input/output (I/O) device drivers 175.

The applications 180 may include one or more programs configured to implement one or more of the various operations and features according to embodiments of the present invention. For example, the applications 180 may include the waveform generator 181 configured to communicate a waveform control signal to one or both of the electrodes 115A, 115B. The applications 180 may also include the measurement system 182 for measuring an impedance or other electrical characteristic (e.g., capacitance) between the electrodes 115A, 115B. In some embodiments, the memory 130 may include additional applications, such as a networking module for connecting to a network. In some embodiments, the waveform generator 181 may be configured to activate at least one electrode (i.e., to control the magnitude, duration, waveform and other attributes of stimulation delivered by the at least one electrode). In some such embodiments, the waveform generator 181 may be configured to activate at least one electrode based upon a prescription from a prescription database, which may include one or more sets of instructions for delivering one or more time-varying waveforms to the vestibular system of a subject.

The data 190 may comprise static and/or dynamic data used by the operating system 170, applications 180, I/O device drivers 175 and/or other software components. The data 190 may include the waveform data 191 including one or more treatment protocols or prescriptions. In some embodiments, the data 190 may further include measurement data 192 including impedance measurements between the electrodes 115A, 115B and/or estimates of electrical contact based on electrical impedance measurements. Electrical impedance measurements may include resistive and capacitive components of the interface between the electrodes 115A, 115B and the ear canal. In some embodiments, the measurement data 192 may include measurements of electrical signals that are produced by the vestibular system. For example, the measurement data 192 may include electrovestibulography signals, or EVestG signals.

I/O device drivers 175 may include software routines accessed through the operating system 170 by the applications 180 to communicate with devices such as I/O circuits 140, memory 130 components and/or the electrodes 115A, 115B.

In some embodiments, the waveform generator 181 may be configured to pass an electrical current through at least one of the electrodes 115A, 115B to stimulate the nervous system and/or the vestibular system of a subject. In particular embodiments, the waveform generator 181 may be configured to pass the electrical current through the at least one electrode 115A, 115B based upon a prescription comprising a set of instructions for delivering one or more time-varying waveforms to the vestibular system of a subject. In some embodiments, the electrical current may be produced in response to an electrical voltage differential provided between the two electrodes 115A, 115B. However, in some embodiments, the waveform generator 181 may be configured to pass two independent electrical currents through the two electrodes 115A, 115B, respectively. The two independent electrical currents may be produced in response to electrical voltage differentials provided between each of the two electrodes 115A, 115B and one or more additional points of electrical contact with the body of the subject.

In some embodiments, the stimulation device 100 may be communicatively connected to at least one electrode 115A, 115B via a conductive line. In some embodiments, the stimulation device 100 may be operatively connected to a plurality of electrodes, and the stimulation device 100 may be operatively connected to each electrode via a separate conductive line.

In some embodiments, the controller 110 may be operatively connected to at least one of the electrodes 115A, 115B via a wireless connection, such as a Bluetooth connection. In some embodiments, the stimulation device 100 may be configured to activate the at least one of the electrodes 115A, 115B to deliver one or more actively controlled, time-varying waveforms to the vestibular system and/or the nervous system of a patient. For example, one or more of the electrodes 115A, 115B may be electrically connected to a wireless receiver and a power source independent of the controller 110. The wireless receiver may receive the wireless signal corresponding to a modulated waveform and may activate the one or more of the electrodes 115A, 115B.

In some embodiments, the stimulation device 100 may include one or more caloric stimulators, 116A, 116B. The simulation device 100 may stimulate a nervous system by providing third and fourth waveforms to the caloric stimulators, 116A, 116B. The caloric stimulation from the caloric stimulators may be combined with the galvanic stimulation from the electrodes 115A, 115B.

In some embodiments, the stimulation device 100 may include one or more speakers, 117A, 117B. The simulation device 100 may provide one or more audio waveforms to the speakers, 117A, 117B. In some embodiments, the stimulation device 100 may include an input connector to receive one or more external audio waveforms that may be provided to the speakers 117A, 117B.

Figure 2:
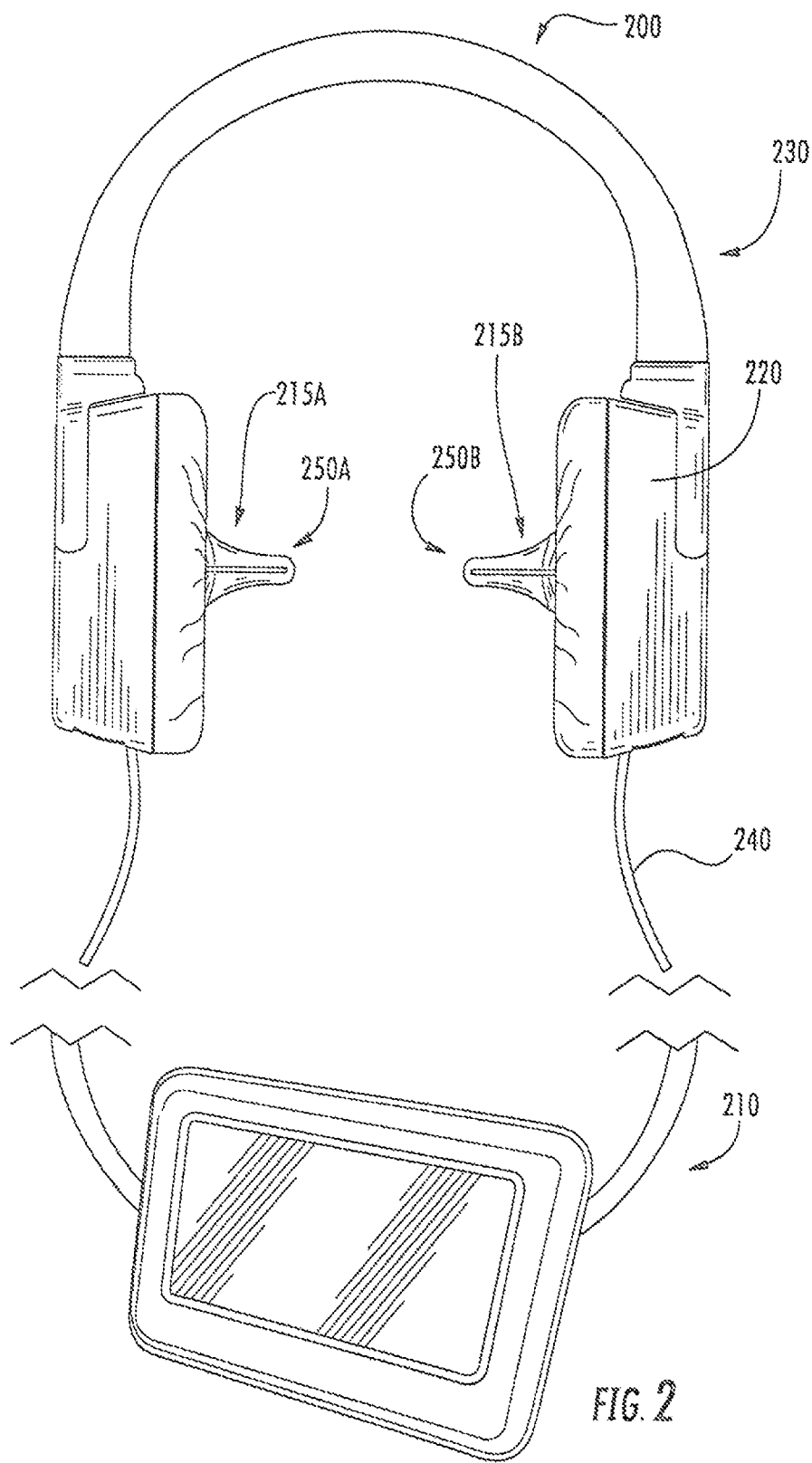
FIG. 2 is a front view illustrating a stimulation device having in-ear electrodes according to some embodiments of the present invention.

FIG. 2 is a front view illustrating a stimulation device according to some embodiments of the present invention. Referring to FIG. 2, a stimulation device 200 may be an in-ear stimulation apparatus. The stimulation device 200 may be similar to the stimulation device 100 illustrated in FIG. 1 except for the differences as noted. The stimulation device 200 may include a support or headband 230, earphones 220, a controller 210 and/or cables 240. In some embodiments, the stimulation device may not include the cables 240 and the controller 210 may connect to the earphones 220 wirelessly. The earphones 220 may include respective electrodes 215A, 215B that are configured to be positioned in the ear of a patient or subject. The electrodes 215A, 215B may be configured to make electrical contact with an inner surface of the ear of the patient or subject such that, when activated, the electrode 215A, 215B may stimulate the vestibular system of the patient or subject.

The electrodes 215A, 215B may be configured as respective earpieces 250A, 250B or may be configured as parts of the respective earpieces 250A, 250B. For example, in some embodiments, an earpiece may be formed primarily of a conductive metal and the entire earpiece 250A, 250B may be an electrode 215A, 215B. In other embodiments, a part of or all of an exterior surface of an earpiece 250A, 250B may be coated with an electrically conductive metal to form the electrode 215A, 215B. In some embodiments, a part of or all of an exterior surface of an earpiece 250A, 250B may be coated with an thin layer of an electrically insulating material that covers the electrode 215A, 215B and electrically insulates the electrode 215A, 215B from the ear of the patient or subject at DC. However, the thin layer of the electrically insulating material may allow higher frequency waveforms to pass through the thin layer of the electrically insulating material from the electrode 215A, 215B to the ear of the patient or subject. For example, in some embodiments, the thin layer of the electrically insulating material may be an anodized finish on an electrically conductive metal. However, in other embodiments, the electrically insulating material may be a thin layer of rubber, plastic, or another insulating material.

In some embodiments, the electrode 215A, 215B may be in electrical contact with the ear canal without directly physically contacting the ear canal. An electrical conduit may be positioned and configured to provide or improve electrical contact between the ear canal and the electrode 215A, 215B. The electrical conduit may be configured to conform to the ear canal, such as a flexible or conformable, electrically conductive material that is configured to increase contact and/or conductivity between the electrode 215A, 215B and the ear canal. The electrically conductive material may be a liquid or solid material or a combination of liquid and solid materials. Moreover, the electrically conductive material may be affixed to the electrode 215A, 215B. For example, in some embodiments, the electrode 215A, 215B may be covered by a porous material that is permeated with an electrically conductive liquid. In some embodiments, the electrode 215A, 215B may be covered with a layer of cotton to avoid direct physical contact with the ear canal. The layer of cotton may be soaked with an electrically conductive liquid, for example a saline solution, to provide the electrical connection between the electrode 215A, 215B and the ear canal. In some embodiments, the electrically conductive liquid may be positioned in the ear canal. The ear canal may be sealed, for example, with an earplug or other sealing material to contain the electrically conductive liquid inside the ear canal. In some embodiments the electrode 215A, 215B and/or an electrical attachment thereto may pass through or around the earplug or other sealing material.

Although the electrodes 215A, 215B are illustrated in FIG. 2 as being integrated with the earpieces 250A, 250B, In some embodiments, the electrodes 215A, 216B may not be configured to fit within an ear cavity. For example, the electrodes 215A, 216B may be configured to contact a portion of the skin next to the ear and over a mastoid part of a temporal bone.

It should be understood that other configurations for supporting the headphones and/or earpieces 250A, 250B may be used, including support bands that are positioned under the chin or over the ear, for example, as may be used with audio earphones. For example, FIG. 3 is a front and side view illustrating a user wearing a stimulation device according to some embodiments of the present invention. Referring to FIG. 3, a stimulation device 200' may be similar to the stimulation devices 100, 200 illustrated in FIGS. 1-2 except for the differences as noted. The stimulation device 200' may include straps 260 and/or headbands 270. In some embodiments, the headbands 270 may provide increased stability of the earphones 220 to provide potentially improved contact of the earpieces 250A, 250B (not shown). In some embodiments, one or more of the straps 260 and/or headbands 270 may provide an additional point of electrical contact to the user, for example a neutral connection to the user.

Although embodiments according to the present invention are illustrated with respect to two ear stimulators in which an electric current is passed from electrode to another through the subject's tissue (e.g., the head), it should be understood that, in some embodiments, the stimulation device 200' may only include one electrode 215. In such embodiments, the stimulation device 200' may provide an electrical stimulus as a voltage between the electrode 215A and an additional point of electrical contact. For example, the additional point of electrical contact may be located on a strap 260 and/or headband 270. In some embodiments, two electrodes 215A, 215B in the ears or on the mastoids may be used with one or more additional points of electrical contact to pass separate electrical currents from each of the electrodes 215A, 215B to the one or more additional points of electrical contact.

Figure 4:
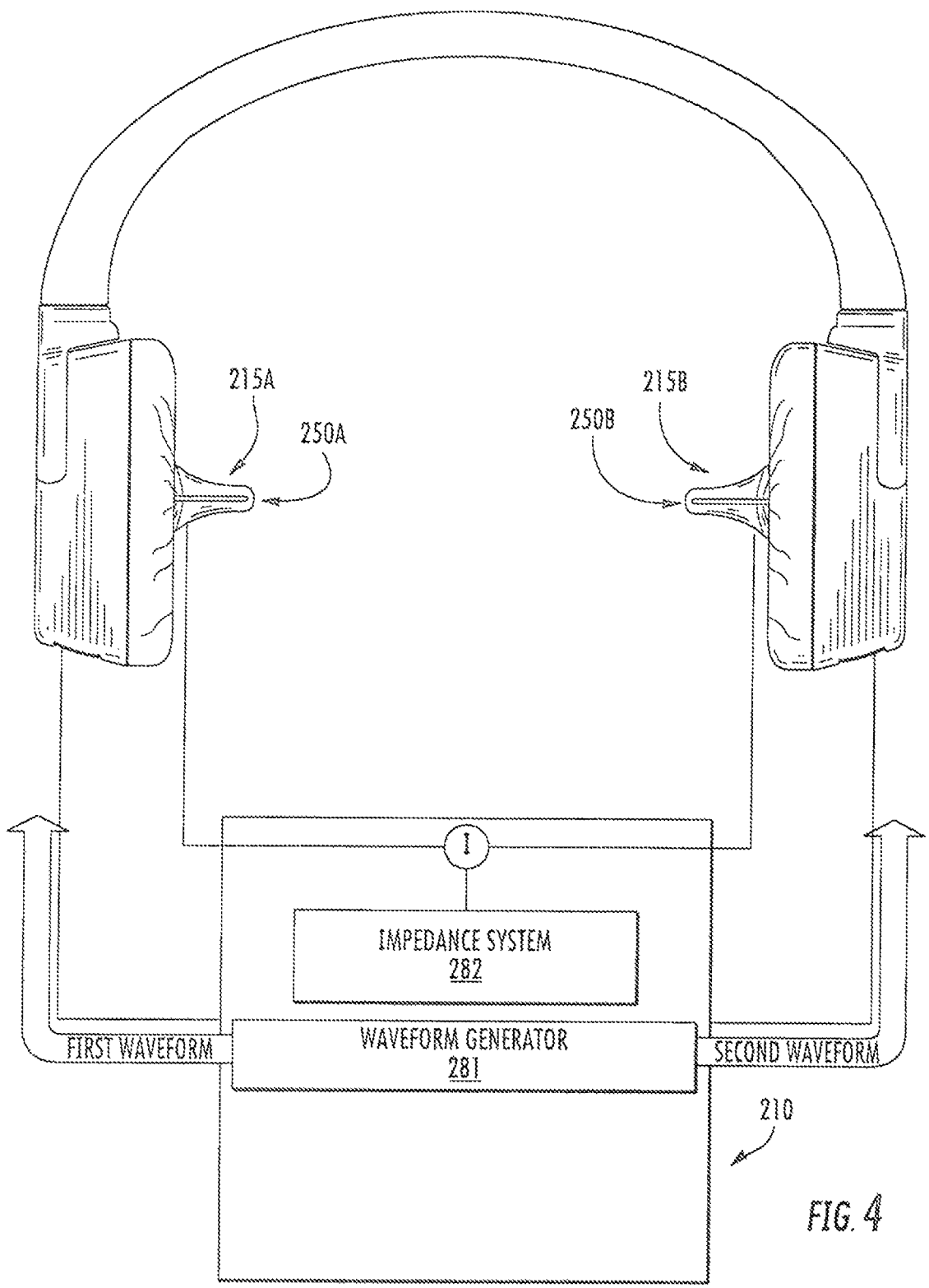
FIG. 4 is a schematic block diagram illustrating a stimulation device according to some embodiments of the present invention.

FIG. 4 is a schematic block diagram illustrating a stimulation device according to some embodiments of the present invention. Referring to FIG. 4, a stimulation device may be similar to the stimulation devices 100, 200 illustrated in FIGS. 1-2 except for the differences as noted. The controller 210 may include a waveform generator 281 and a measurement system 282 that may be similar to the waveform generator 181 and the measurement system 182 of FIG. 1, except for differences as noted. The waveform generator 281 may be configured to communicate first and second waveforms to the electrodes 215A, 215B. It should be understood that the first and second waveforms may be the same, or in some embodiments, the first and second waveforms may be different such that the output delivered from the electrodes 215A, 215B may be independently controlled and may be different from one another.

As illustrated in FIG. 4, in some embodiments, the measurement system 282 may deliver an electrical current to one or more of the electrodes 215A, 215B. In this configuration, the impedance and/or capacitance value between the electrodes 215A, 215B may be used to monitor the electrical contact between the electrodes 215A, 215B. In some embodiments, impedance and/or capacitance values may be detected for a range of subjects to determine a range of impedance and/or capacitance values in which it may be assumed that the electrodes 215A, 215B are in sufficient electrical contact with the subject's ear canal. When a headset is being fitted to a new patient, the impedance and/or capacitance between the electrodes 215A, 215B may be detected, and if the impedance value is within the acceptable range, it may be assumed that there is good electrical contact between the electrodes 215A, 215B and the subject's ear canal.

In some embodiments, when the headset is being fitted to a new patient, the impedance and/or capacitance value between electrodes 215A, 215B may be detected and used as a patient specific baseline to determine if the patient is later using the headset and a proper configuration. For example, the patient may use a headset according to embodiments of the present invention in a setting that may or may not be supervised by a medical professional. In either environment, the measurement system 282 may record an impedance and/or capacitance value at a time that is close in time or overlapping with the time in which the treatment waveforms are delivered to the electrodes 215A, 215B. The medical health professional or the measurement system 282 may analyze the impedance value to determine whether the electrodes 215A, 215B were properly fitting during treatment. In some embodiments, the measurement system 282 may be configured to provide feedback to the user when impedance values detected that are inconsistent with properly fitting electrodes 215A, 215B in good electrical contact with the ear canal. In this configuration, the measurement system 282 may provide a degree of electrical contact between the electrodes 215A, 215B and the ear canal in real-time or in data recorded and analyzed at a later time. Accordingly, patient compliance with treatment protocols may be monitored based on the detected impedance during or close in time to treatment.

In some embodiments, the impedance may be calculated based separately for each of the electrodes 215A, 215B. For example, in some embodiments, an impedance may be measured between ones of the electrodes 215A, 215B and an additional point of connection located on a strap 260 and/or headband 270, as illustrated in FIG. 3.

In particular embodiments, the measurement system 282 may also provide feedback to the waveform generator 281, for example, so that the waveform generator 281 may increase or decrease an amplitude of the waveform control signal responsive to the degree of electrical contact determined by the measurement system 282 based on the impedance and/or capacitance value. For example, if the measurement system 282 determines based on the impedance value that there is a poor fit and poor electrical contact with the ear canal, then the waveform generator 281 may increase an amplitude of the output to the electrodes 215A, 215B to compensate for the poor electrical contact. In some embodiments, the measurement system 282 may determine patient compliance, e.g., whether the patient was actually using the device during administration of the waveforms.

Although embodiments of the present invention are illustrated with respect to two electrodes 215A, 215B, it should be understood that in some embodiments, a single electrode 215A may be used, and an electrical contact may be affixed to another location on the user's head instead of the second earpiece 250B to thereby provide an electrical circuit for determining impedance values and estimating thermal contact as described herein.

In some embodiments, the measurement system 282 may measure one or more impedance value based on the current and voltage levels of the first and second waveforms. In some embodiments, the measurement system 282 may include hardware to measure the current and/or voltage levels of the first and second waveforms. For example, the measurement system 282 may calculate an impedance by dividing a voltage level by a current level. In such embodiments, the measurement system 282 may calculate an impedance value while the waveform generator 281 generates the first and second waveforms.

In some embodiments, the measurement system 282 may measure one or more electrical signals that are produced by the vestibular system. For example, the measurement system 282 may measure electrovestibulography, or EVestG, signals. EVestG signals may be useful to determine an efficacy of a treatment. For example, EVestG signals may be useful in determining a presence and/or degree of one or more disorders. Accordingly, an efficacy of a treatment may be monitored based on feedback provided by the measured EVestG signals during or close in time to treatment. In some embodiments, a treatment may be revised and/or discontinued based on measured EVestG signals.

FIG. 5A is a schematic block diagram illustrating a stimulation device according to some embodiments of the present invention. Referring to FIG. 5A, a stimulation device 500 may be similar to the stimulation device 100 illustrated in FIGS. 1-4 except for the differences as noted. For example, the stimulation device may include a controller 510A and electrodes 515A, 515B that may be similar to the controller 210 and electrodes 215A, 215B of FIGS. 1-4, except for differences as noted. The stimulation device may include earphones including earpieces 550A, 550B including the electrodes 515A, 515B. The earphones may further include thermal electric devices, "TEDs," attached to the earpieces 550A, 550B. The controller 510A may include a galvanic waveform generator 581A that may be similar to the waveform generator 281 of FIGS. 1-4. The controller 510A may also include a caloric waveform generator 581B. The caloric waveform generator 518B may be configured to activate the TEDs attached to the earpieces 550A, 550B. In this configuration, caloric vestibular stimulation may be administered to a subject via the subject's ear canal. Administration of caloric vestibular stimulation using earpieces is discussed in U.S. patent application Ser. No. 12/970,312, filed Dec. 16, 2010, U.S. patent application Ser. No. 12/970,347, filed Dec. 16, 2010, U.S. patent application Ser. No. 13/525,817, filed Jun. 18, 2012, and U.S. patent application Ser. No. 13/994,266, filed May 15, 2014, the disclosures of which are hereby incorporated by reference in their entirety.

In some embodiments, the galvanic waveform generator 581A may deliver first and second waveforms to the electrodes 515A, 515B and the caloric waveform generator may deliver third and fourth waveforms to the TEDs attached to the electrodes 515A, 515B, respectively. In some embodiments, the galvanic waveform generator 581A may deliver first and second waveforms and the caloric waveform generator may deliver third and fourth waveforms simultaneously. In such embodiments, the stimulation device may deliver galvanic vestibular stimulation and caloric vestibular stimulation. In some embodiments, the galvanic vestibular stimulation may enhance a delivery of the caloric vestibular stimulation.

Figure 5B:
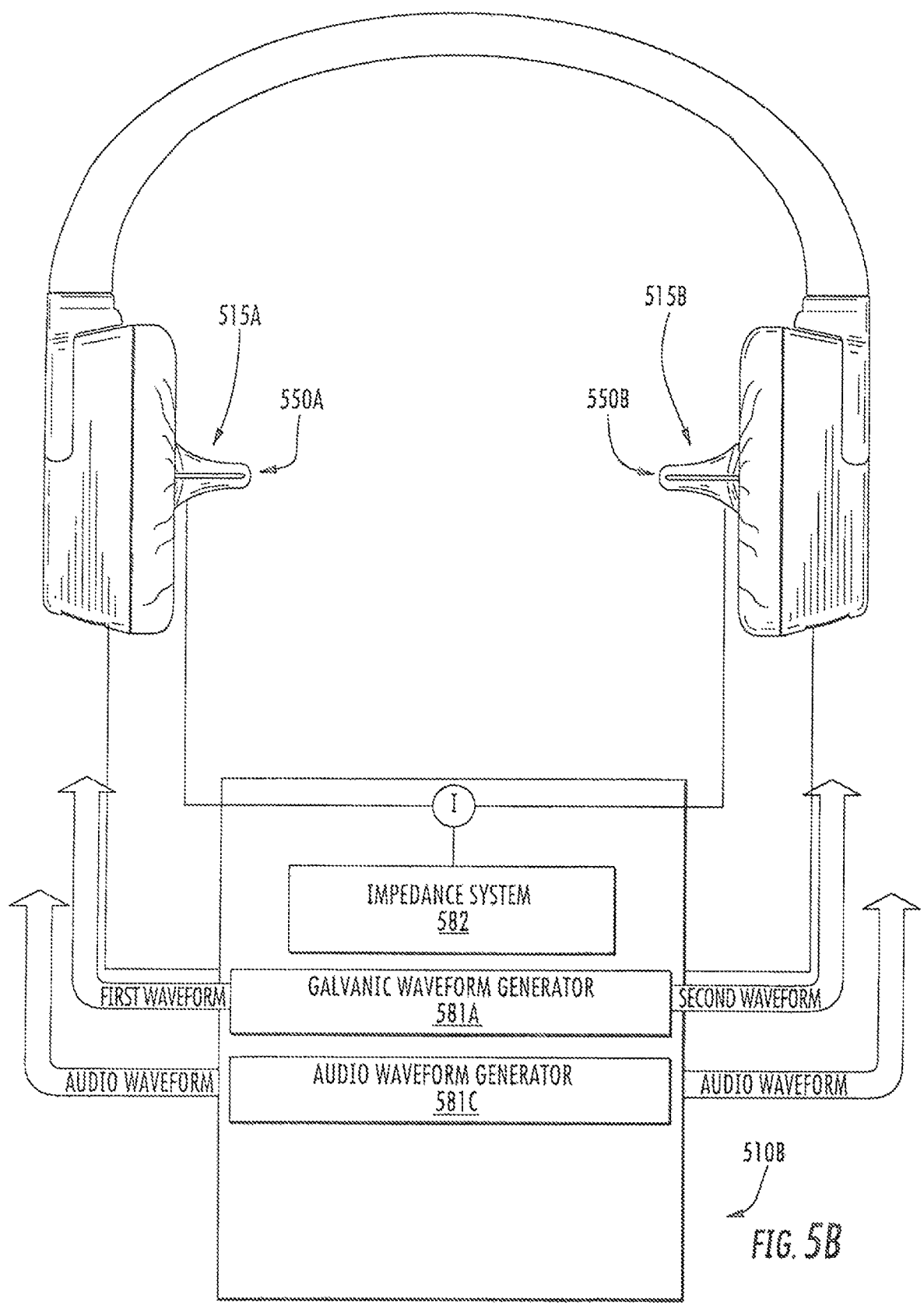

FIG. 5B is a schematic block diagram illustrating a stimulation device according to some embodiments of the present invention. Referring to FIG. 5B, a stimulation device may be similar to the stimulation device 100 illustrated in FIGS. 1-4 except for the differences as noted. For example, the stimulation device may include a controller 510B and electrodes 515A, 515B that may be similar to the controller 210 and electrodes 215A, 215B of FIGS. 1-4, except for differences as noted. The stimulation device 500 may include earphones including earpieces 550A, 550B including the electrodes 515A, 515B. The earphones may further include speakers attached to the earpieces 550A, 550B. In some embodiments, the speakers may be included in the earpieces, 550A, 515B. In other embodiments, the earpieces 550A, 550B may include a tube or other channel of air that conducts sound from externally attached speakers to the inner ear. In yet other embodiments, the stimulation device 500 may include bone conduction speakers and the earpieces 550A, 550B may conduct vibrations from the bone conduction speakers to bones that are adjacent to the ear canals.

In some embodiments, the galvanic waveform generator 581A may deliver first and second waveforms to the electrodes 515A, 515B and the audio waveform generator may deliver audio waveforms to the speakers attached to the electrodes 515A, 515B, respectively. In some embodiments, the galvanic waveform generator 581A may deliver first and second waveforms and the audio waveform generator may deliver audio waveforms simultaneously. In such embodiments, the stimulation device 500 may deliver galvanic vestibular stimulation and audio stimulation. As used herein, an audio waveform is a waveform that includes frequency components that are within a hearing range of the subject. For example, an audio waveform may include frequency components within a range of about 20 to 20,000 Hz. In some embodiments, the audio waveforms may be time-varying and/or may include one or more patterns. For example, the audio waveforms may include music and/or voice. In some embodiments, the waveforms of the galvanic vestibular stimulation may be modulated based on the audio waveforms.

For example, in some embodiments, the first and/or second waveforms of the galvanic vestibular stimulation may include a carrier function having a frequency that may be sufficiently high to produce the lower impedance that permits transmission through the skin. The audio waveforms may include one or more frequencies that are lower than the frequency of the carrier function. One or more parameters of the carrier function may be modulated according to the one or more lower frequencies of the audio waveforms. For example, one or more of the amplitude and frequency of the carrier function may be modulated to produce the first and/or second waveforms of the galvanic vestibular stimulation. In other embodiments, the first and/or second waveforms of the galvanic vestibular stimulation may be directly proportional to the audio waveforms.

Figure 6B:
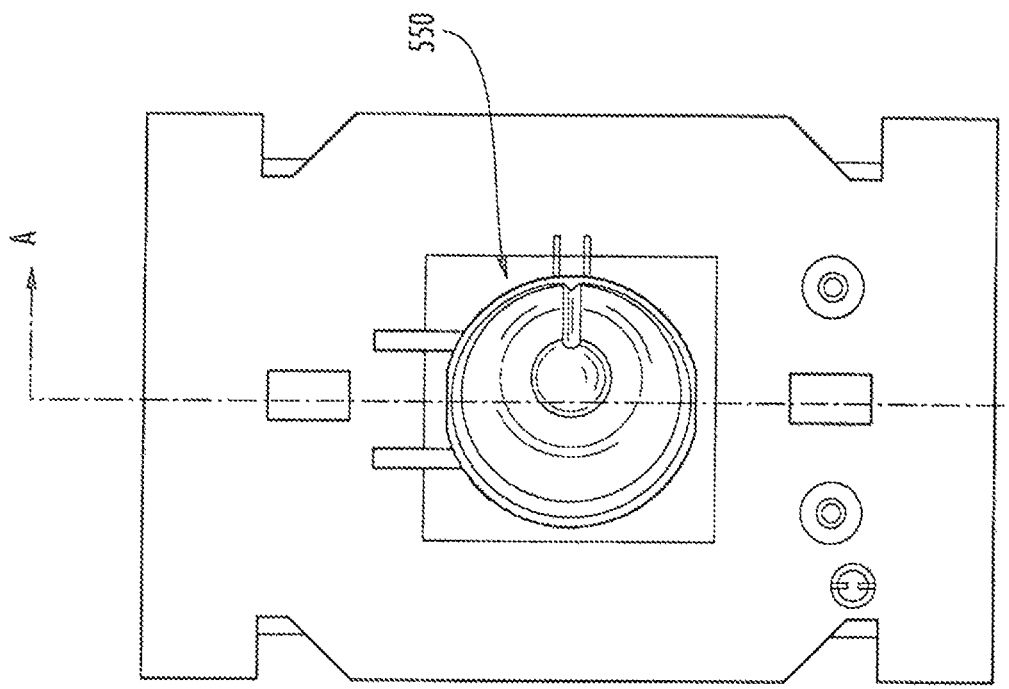
FIG. 6B is a cross-sectional view schematically illustrating the earpiece of FIG. 6A.
Figure 6A:
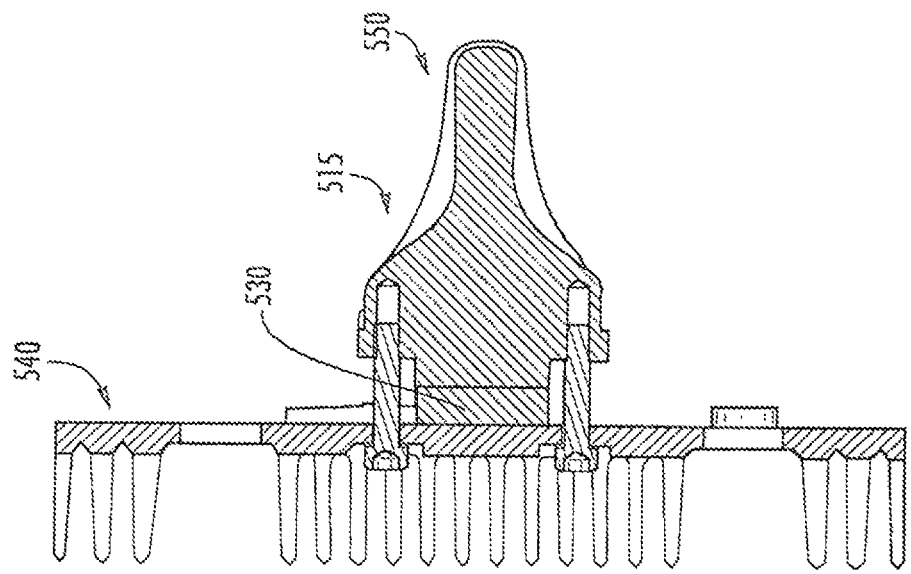
FIG. 6A is a front perspective view illustrating an earpiece of the stimulation device of FIG. 5.

FIG. 6A is a front perspective view illustrating an earpiece of the stimulation device of FIG. 5A. FIG. 6B is a cross-sectional view schematically illustrating the earpiece of FIG. 6A. Referring to FIGS. 6A-6B and FIG. 5A, an earpiece 550 may include an electrode 515. As noted above, the electrode 515 may form all, part of, or a coating on the surface of the earpiece 550. A thermoelectric device 530 may be coupled between the earpiece 550 and a heatsink 540.

The electrode 515 may receive a first or second electrical waveform from the galvanic waveform generator 581A of the controller 510A. The electrode 515 may be electrically conductive. For example, the electrode 515 may be formed of an electrically conductive metal. The electrode 515 may be formed to fit in an ear canal and provide an electrical interface to the ear canal. Thus, the galvanic waveform generator 581A may provide a galvanic stimulus to stimulate the nervous system and/or vestibular system of the subject based on the first or second waveform delivered through the electrical connection between the electrode 515 and the ear canal.

In some embodiments, the electrode 515 may be in electrical contact with the ear canal without directly physically contacting the ear canal. An electrical conduit may be positioned and configured to provide or improve electrical contact between the ear canal and the electrode 515. The electrical conduit may be configured to conform to the ear canal, such as a flexible or conformable, electrically conductive material that is configured to increase contact and/or conductivity between the electrode 515 and the ear canal. The electrically conductive material may be a liquid or solid material or a combination of liquid and solid materials. Moreover, the electrically conductive material may be affixed to the electrode 515. For example, in some embodiments, the electrode 515 may be covered by a porous material that is permeated with an electrically conductive liquid. In some embodiments, the electrode 515 may be covered with a layer of cotton to avoid direct physical contact with the ear canal. The layer of cotton may be soaked with an electrically conductive liquid, for example a saline solution, to provide the electrical connection between the electrode 515 and the ear canal. In some embodiments, the electrically conductive liquid may be positioned in the ear canal. The ear canal may be sealed, for example, with an earplug or other sealing material to contain the electrically conductive liquid inside the ear canal. In some embodiments the electrode 515 and/or an electrical attachment thereto may pass through or around the earplug or other sealing material.

The thermoelectric device 530 may receive a third or fourth thermal waveform from the caloric waveform generator 581B. The thermoelectric device 530 may provide a temperature differential between the earpiece 550 and the heatsink 540 based on the third or fourth waveform. The earpiece 550 and/or the electrode 515 of the earpiece 550 may provide a thermal interface between the thermoelectric device 530 and the ear canal. Thus, the caloric waveform generator 581B may provide a caloric stimulus to stimulate the nervous system and/or vestibular system of the subject based on the third or fourth waveform delivered through the thermal interface between the electrode 515 and the ear canal.

Figure 7:
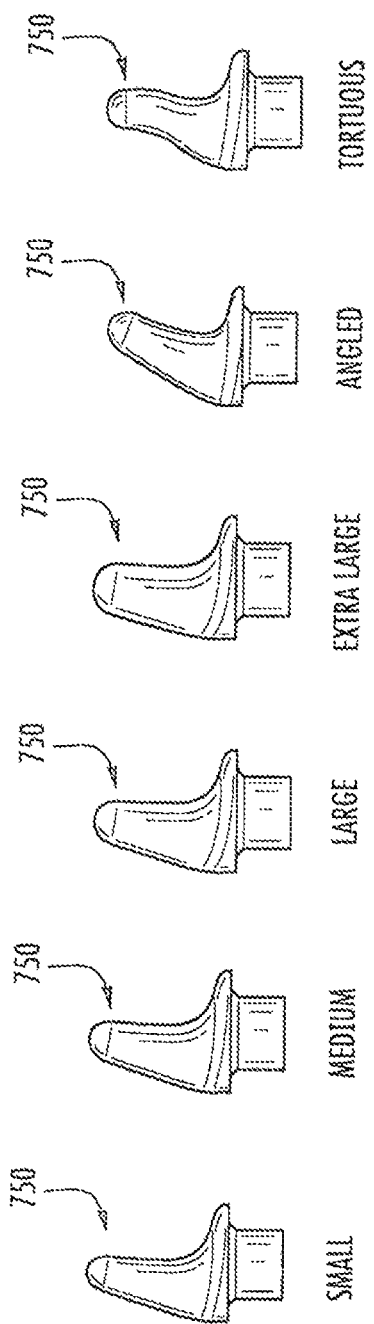
FIG. 7 is a side view illustrating various alternative shapes and sizes of earpieces of stimulation devices according to some embodiments of the present invention.

FIG. 7 is a side view illustrating various alternative shapes and sizes of earpieces of stimulation devices according to some embodiments of the present invention. Referring to FIG. 7, an earpiece 750 may be similar to the earpieces illustrated in FIGS. 2-6 except for the differences as noted. A shape and/or size of the earpiece 750 may be selected to optimize the electrical and/or thermal connection. The shape and/or size of the earpiece 750 may be selected for optimal comfort of the subject. In some embodiments, the earpiece 750 may be user replaceable, however embodiments of the present invention are not limited thereto. For example, in some embodiments, the earpiece 750 may be permanently attached to a TED and/or earphone. In some embodiments, a size of the earpiece 750 may be selected according to a size of the ear canal of the subject. For example, the earpiece 750 may be small, medium, large, or extra large. In some embodiments, a shape of the earpiece 750 may be selected based upon a shape of the ear canal of the subject. For example, the earpiece 750 may be angled and/or tortuous (twisted or curved) with respect to a base of the earpiece 750. However, the present invention is not limited to the illustrated shapes and sizes.

Figure 8:
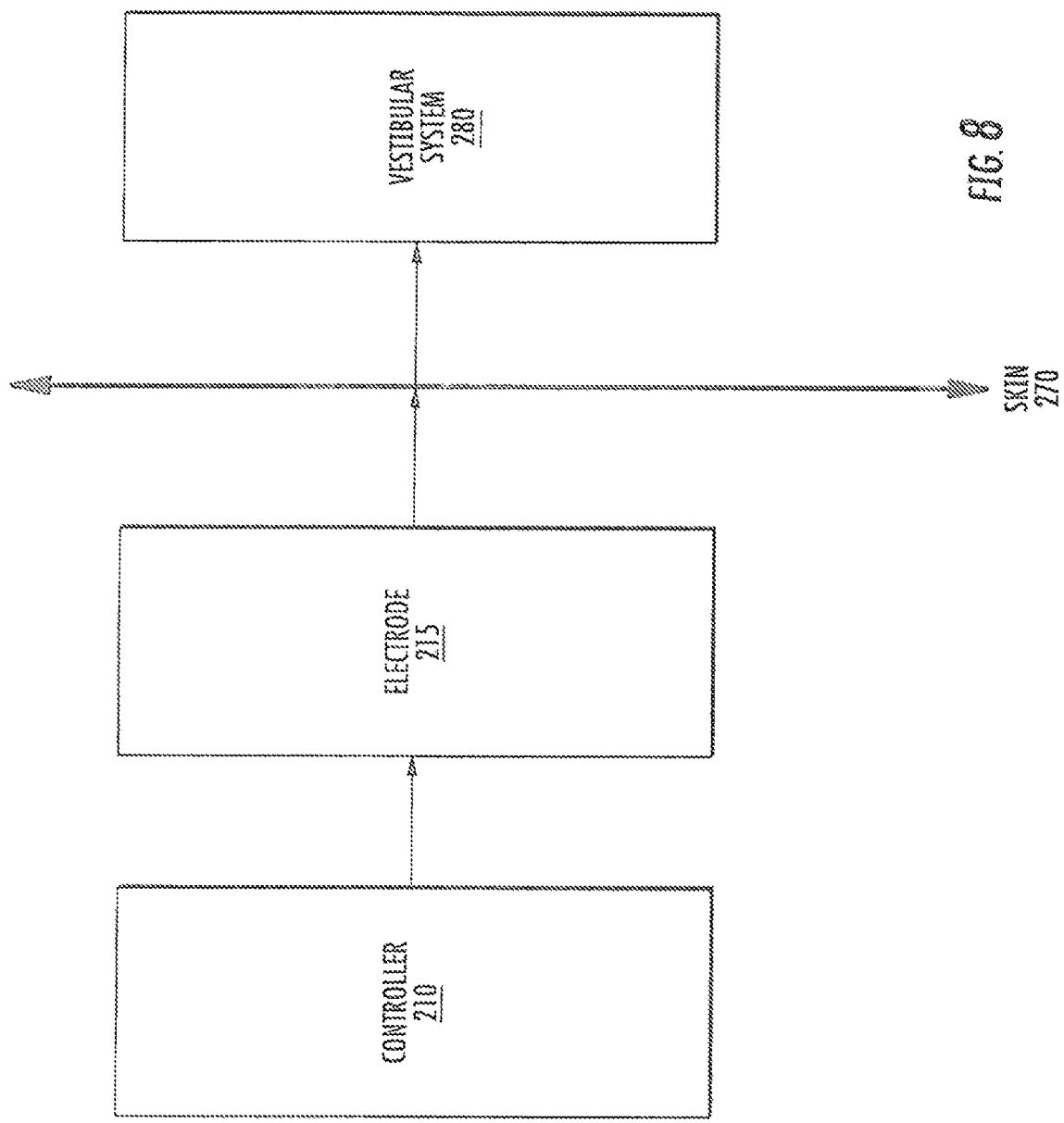
FIG. 8 is a schematic diagram illustrating a path of a stimulation signal for an externally applied stimulation signal according to some embodiments of the present invention.

FIG. 8 is a schematic diagram illustrating a path of a stimulation signal according to some embodiments of the present invention. Referring to FIG. 8, a path of a stimulation signal according to some embodiments of the present invention may include the controller 210, an electrode 215, skin, and the vestibular system. The controller 210 may be the controller 210 as described above with reference to FIGS. 2-4. The electrode 215 may be one or more of the electrodes 215A, 215B, as described above with reference to FIGS. 2-4. The electrode 215 may be in physical and electrical contact with the skin of a subject. For example, the electrode 215 may be inserted into an ear canal of the subject and may be in physical and electrical contact with a portion of the skin lining the ear canal of the subject.

Figure 9:
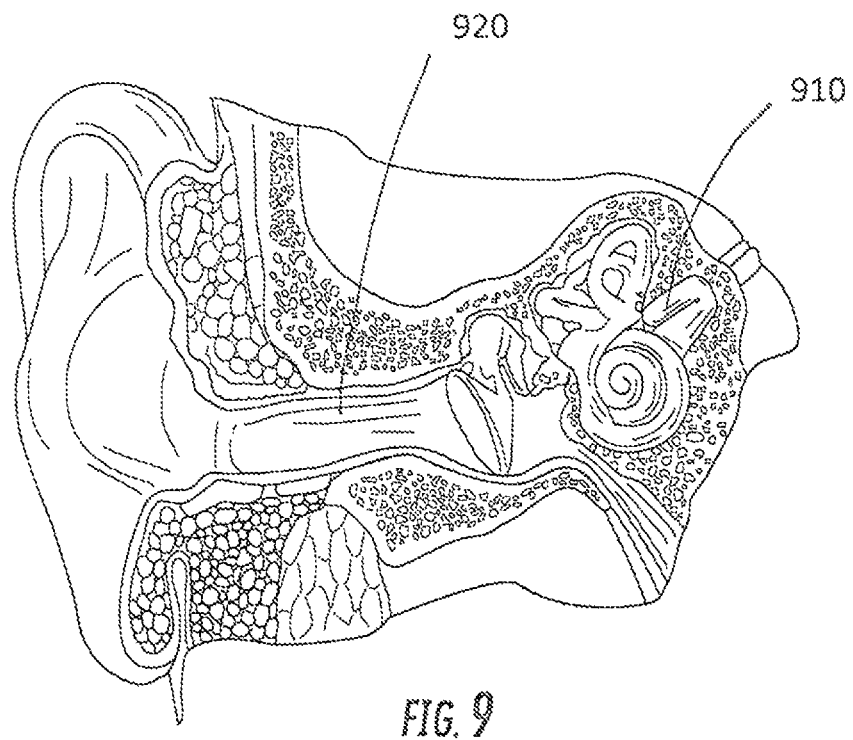
FIG. 9 is a cross-sectional view schematically illustrating an ear and surrounding portions of a human body.
Figure 10:
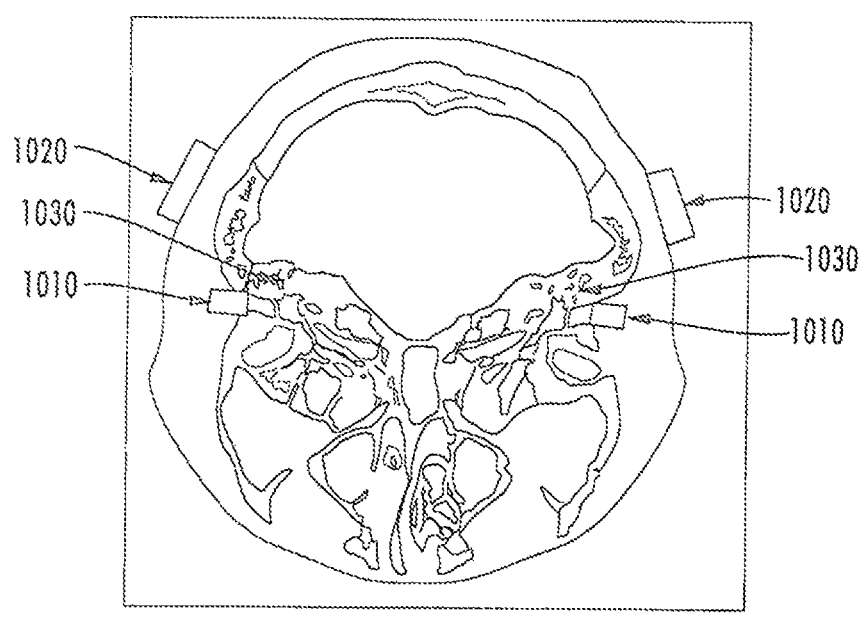
FIG. 10 is a cross-sectional view schematically illustrating relative placements of electrodes with respect to a computerized tomography scan of a human head.

FIG. 9 is a cross-sectional view schematically illustrating an ear and surrounding portions of a human body. Referring to FIG. 9, a vestibular nerve 910 of the vestibular system may be in proximity to an ear canal 920. FIG. 10 is a cross-sectional view schematically illustrating relative placements of electrodes with respect to a computerized tomography scan of a human head. Referring to FIG. 10, an electrode 1010 contacting a portion of the skin lining the ear canal may be in closer proximity to a vestibular nerve 1030 (approximate location shown) than an electrode 1020 contacting the skin next to the ear and over a mastoid part of a temporal bone. Referring to FIGS. 8-10, an electrode 215 inserted into an ear canal of the subject may be in close proximity to a vestibular nerve.

Referring again to FIGS. 8 and 2-4, the waveform generator 281 of the controller 210 may electrically stimulate the vestibular system based on a waveform. The waveform may be an electrical signal. The electrical signal may be modulated. The waveform generator 281 may provide the modulated electrical signal to the electrode 215. In some embodiments, the waveform generator 281 may be electrically connected the electrode 215, although the embodiments of the present invention are not limited thereto. For example, in some embodiments, the waveform generator 281 may be wirelessly in communication with an earpiece 250A, 250B that may generate and provide the electrical signal to the electrode 215.

The electrode 215 may provide the electrical signal to the vestibular system. For example, the electrode 215 may provide the electrical signal to the vestibular system via an electrical connection through the skin. The skin may provide an electrical resistance in the electrical path between the electrode and the vestibular system. Thus, the waveform generator 281 may control an amplitude of the waveform such that an amplitude of the electrical signal is sufficient to traverse the skin and stimulate the vestibular system. In some embodiments, the waveform may be modulated based on a frequency.

Figure 11:
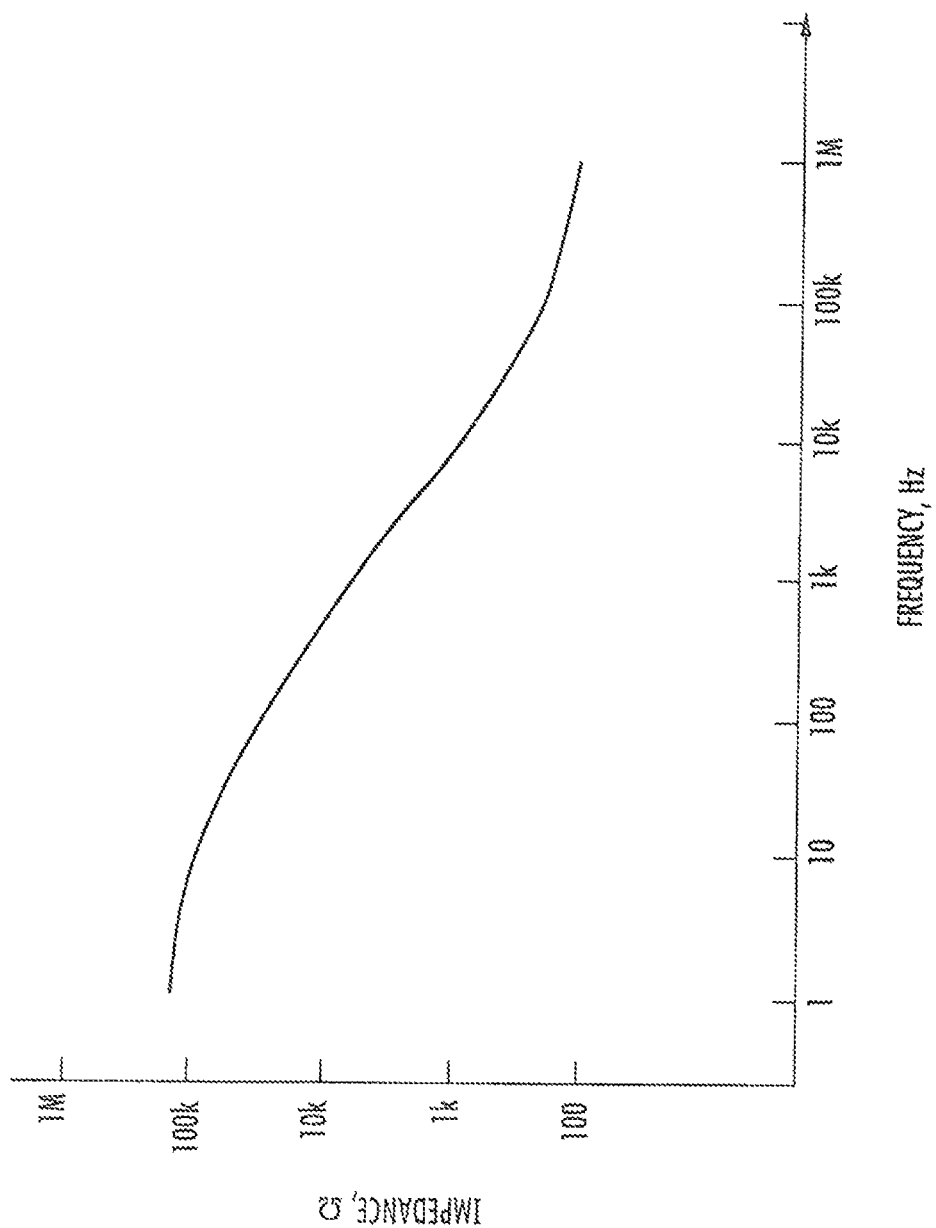
FIG. 11 is a graph illustrating a relationship between an impedance of skin and a frequency of a stimulation waveform according to some embodiments of the present invention.

FIG. 11 is a graph illustrating a relationship between an impedance of skin and a frequency of a stimulation waveform according to some embodiments of the present invention. Referring to FIGS. 8 and 11, an impedance of the skin may decrease as a frequency of the waveform increases. See, e.g., J. Rosell, J. Colominas, P. Riu, R. Pallas-Areny, J. G. Webster, Skin impedance from 1 Hz to 1 MHz, *IEEE Trans Biomed Eng* 35, 649-651 (1988); published online EpubAug (10.1109/10.4599).

For example, at a frequency of 0 Hz, in other words a direct current of a fixed amplitude, the skin may provide a large impedance in the electrical path between the electrode and the vestibular system. Thus, in order to stimulate the vestibular system at a frequency of 0 Hz, the waveform generator 281 may provide a waveform of large amplitude and, accordingly, the electrode may provide an electrical signal with a large voltage. This may not be desired as the subject may experience discomfort, pain, and/or physical damage based on the large voltage.

At higher frequencies, the skin may provide a lower impedance in the electrical path between the electrode and the vestibular system. Thus, in order to stimulate the vestibular system at higher frequencies, the waveform generator 281 may provide a waveform of smaller amplitude and, accordingly, the electrode may provide an electrical signal with a smaller voltage. At the lower voltage, the subject may not experience the discomfort, pain, and/or physical damage. However, the higher frequency may not induce the desired diagnostic and/or therapeutic effects of galvanic vestibular stimulation. For example, some diagnostic and/or therapeutic uses of galvanic vestibular stimulation desire stimulation at a lower frequency. In some embodiments of the present invention, a modulation scheme is provided that generates an electrical signal with a higher frequency to produce the lower impedance and that stimulates the vestibular system at a lower frequency.

Figure 17:
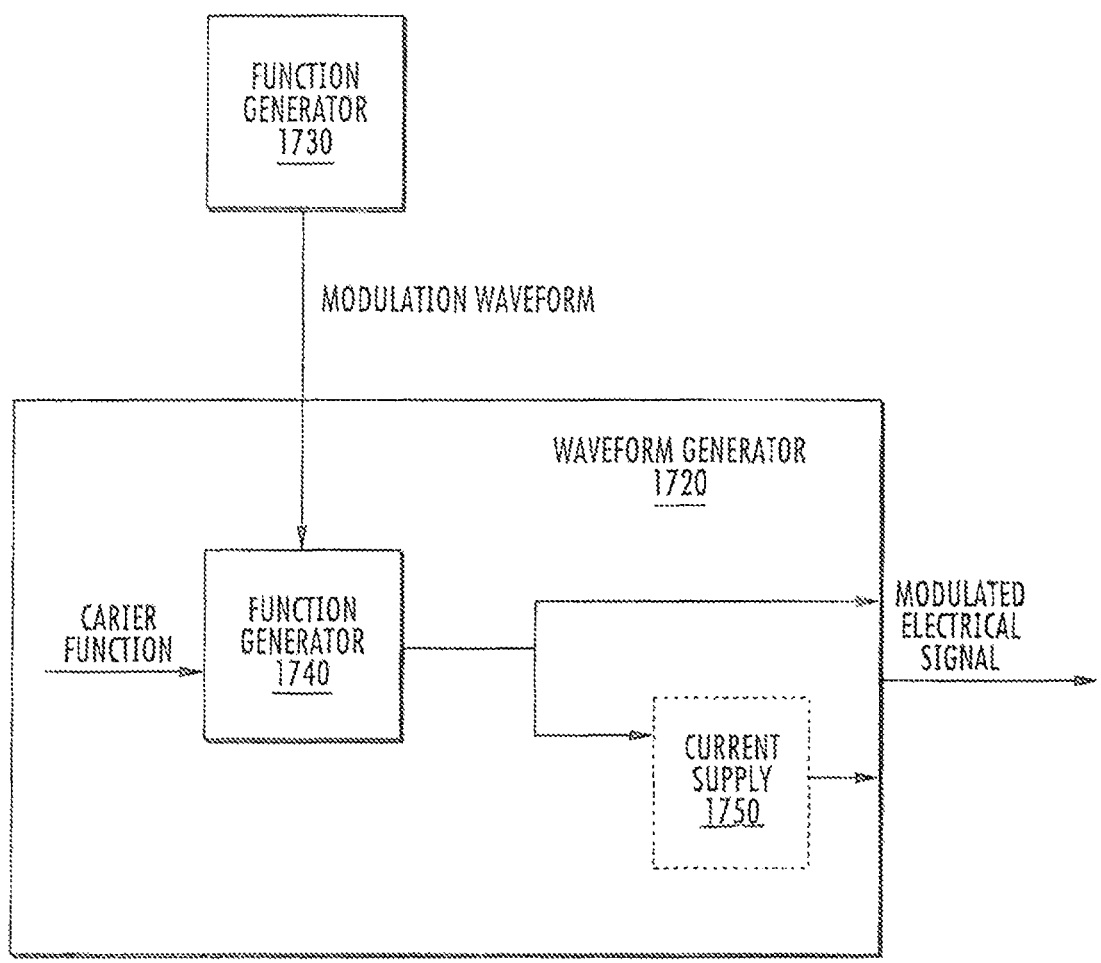
FIG. 17 is a schematic block diagram illustrating portions of a controller according to some embodiments of the present invention.

FIG. 17 is a schematic block diagram illustrating portions of a controller according to some embodiments of the present invention. Referring to FIG. 17, a controller 1710 may be similar to the one or more of the controllers 210, 510A, 510B of FIGS. 4-5B except for the differences as noted. The controller 1710 may include a waveform generator 1720 that may generate the modulated electrical signal based on a time-varying modulation waveform. The waveform generator may receive the modulation waveform from a first function generator 1730. The first function generator 1730 may define the modulation waveform and provide the modulation waveform as a modulated voltage to the waveform generator 1720. The waveform generator 1720 may include a second function generator 1740. The second function generator 1740 may receive a carrier function and the modulation waveform. The second function generator 1740 may modulate the carrier function based on the modulation waveform. For example, the second function generator 1740 may perform frequency modulation or amplitude modulation to generate a voltage-based modulated electrical signal. In some embodiments, the voltage-based modulated electrical signal may be received by a current supply 1750 that produces a clamped current output that may be provided to the first and second electrodes as the modulated electrical signal.

Packet-Based Modulation

Figure 12:
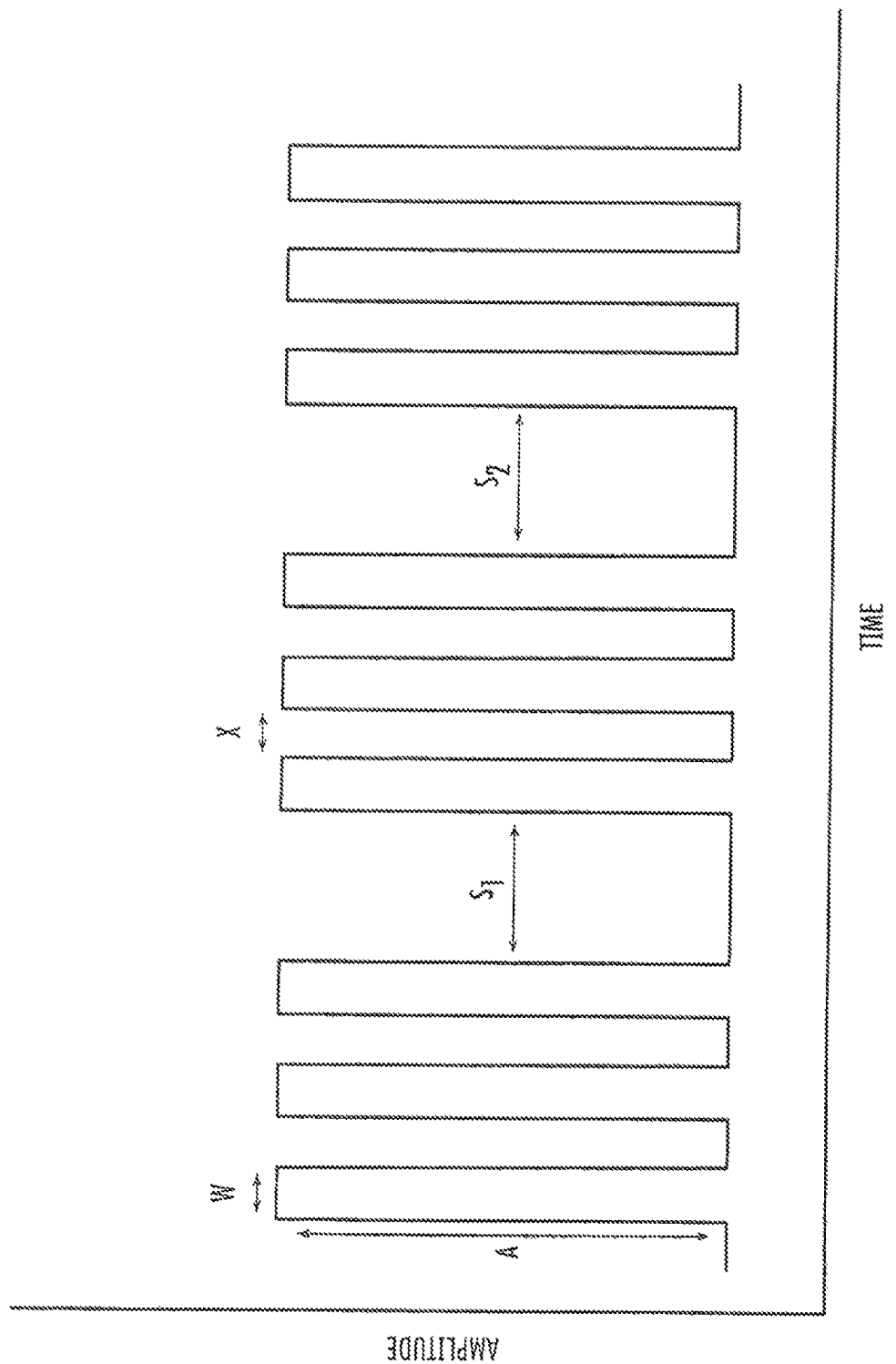
FIG. 12 is a graph illustrating modulated stimulation waveform according to some embodiments of the present invention.

FIG. 12 is a graph illustrating modulated stimulation waveform according to some embodiments of the present invention. Referring to FIG. 12, a waveform may include a plurality of spaced-apart packets of pulses. The pulses may correspond to electrical pulses produced based on the waveform.

Ones of the plurality of packets may include a quantity, N, of pulses and a separation in time, S, between adjacent ones of the plurality of packets of pulses. For example, as illustrated in FIG. 12, the packets may each include a quantity, N, of 3 pulses, although the present invention is not limited thereto. For example, the quantity, N, of pulses may be more or less than three but, in some embodiments, may be at least 2. The separation in time, S, between adjacent ones of the plurality of packets may be defined as a quantity of time between an end of a last pulse of one packet and a beginning of the first pulse of the next adjacent packet.

Ones of the pulses may include a width in time, W, an amplitude, A, and a separation in time, X, between adjacent ones of the pulses within a packet. The width in time, W, of a pulse may be defined as a quantity of time between a rising edge and a falling edge of a single pulse, although the present invention is not limited thereto. The amplitude, A, of the waveform may correspond to the amplitude of the voltage of the electrical signal provided by the electrode 215 of FIG. 8. The separation in time, X, between adjacent ones of the pulses within a packet may be defined as a quantity of time between an end of one pulse within a packet and a beginning of the next pulse within the same packet.

An impedance provided by the skin of FIG. 8 in response to an electrical signal corresponding to the stimulation waveform may be based on the width in time, W, of the pulses and the separation in time, X, between adjacent ones of the pulses within a packet. For example, the width, W, and separation, X, may define a time period of a pulse. A frequency of the pulses may be the inverse of the time period. The impedance may be inversely proportional to the frequency of the pulses, as illustrated in FIG. 11. Thus, the width, W, and separation, X, may be selected to be smaller to provide a higher frequency and, thus, a lower impedance.

At least one of the quantity, N, of the plurality of pulses within ones of the plurality of packets of pulses, the width in time, W, of the plurality of electrical pulses within ones of the plurality of packets of pulses, the amplitude, A, of the plurality of pulses within ones of the plurality of packets of pulses, the separation in time, X, between adjacent ones of the plurality of pulses within ones of the plurality of packets of pulses, and the separation in time, S, between adjacent ones of the plurality of packets of pulses may be modulated to modulate the stimulation waveform. The at least one modulated parameter may be modulated based on a target stimulus frequency. Referring to FIGS. 8 and 10, the vestibular system may be stimulated based on the target stimulus frequency. Thus, the target stimulus frequency may be selected to be low based on the desired diagnostic and/or therapeutic uses of the galvanic vestibular stimulation.

In some embodiments, the separation in time, S, between adjacent ones of the plurality of packets of pulses may be modulated to modulate the stimulation waveform. In other words, the separation in time, S, may not be constant and may be varied based on the target stimulus frequency. For example, the separation in time, $S_1$ between the first packet and the second packet illustrated in FIG. 12 may be different from the separation in time, $S_2$ between the second packet and the third packet illustrated in FIG. 12.

Figure 13:
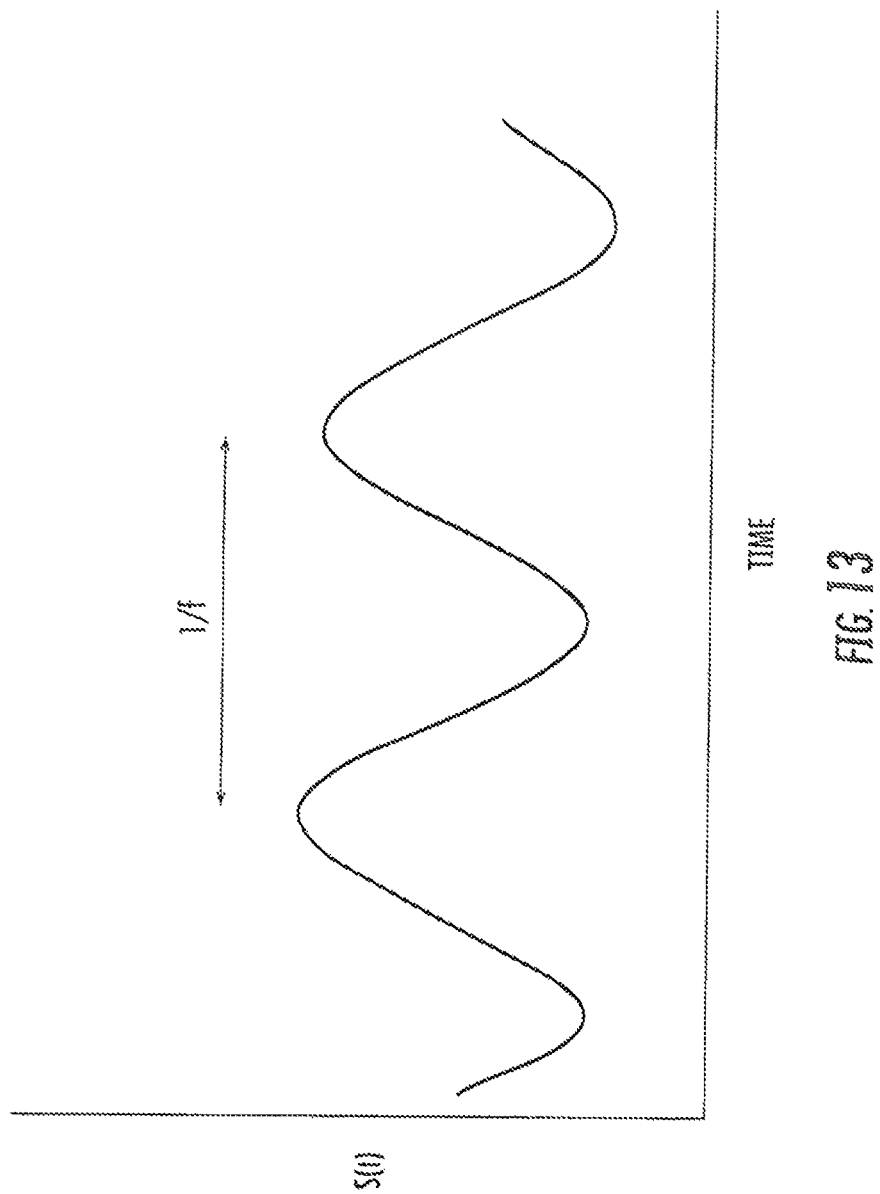
FIG. 13 is a graph illustrating a modulated separation in time between adjacent ones of a plurality of packets of electrical pulses according to some embodiments of the present invention.

FIG. 13 is a graph illustrating a modulated separation in time between adjacent ones of a plurality of packets of electrical pulses according to some embodiments of the present invention. Referring to FIGS. 12 and 13, the separation in time, S, between adjacent ones of the plurality of packets of pulses may be varied in a sinusoidal modulation. The separation in time, S, may vary between a minimum separation value and a maximum separation value. A period of the sinusoidal modulation may define the stimulation frequency. For example, a duration in time between minimum values or between maximum values may define the period. The stimulation frequency may be defined as the inverse of the period. Thus, the separation in time, S, may be varied in a sinusoidal modulation to stimulate the vestibular system based on the target stimulation frequency.

Target neurons of the vestibular system may require a minimum amount of time after stimulation to recover. The target neurons may be stimulated by each pulse. Because the separation in time, X, between pulses within a packet may be selected to be small to provide decreased impedance, the target neurons may not recover between pulses within a packet. Thus, the target neurons may be constantly stimulated within a duration of a packet of pulses. However, the minimum value of the separation in time, S, between packets may be selected to be sufficiently large to allow target neurons to recover before being activated by the next packet of pulses. Thus, by modulating the separation in time, S, the stimulation of the target neurons may be modulated based on the target stimulus frequency. See, e.g., M. W. Bagnall, L. E. McElvain, M. Faulstich, S. du Lac, Frequency-independent synaptic transmission supports a linear vestibular behavior. *Neuron* 60, 343-352 (2008); published online EpubOct 23 (S0896-6273(08)00845-3 [pii]10.1016/j.neuron.2008.10.002) (discussing recovery of vestibular afferent synapse after stimulus trains).

The galvanic vestibular stimulation may have downstream effects in other portions of the brain of the subject based on the target stimulus frequency. In some embodiments, a frequency of the modulated signal may be selected to induce brain rhythms in a target portion of the brain. In some embodiments, the galvanic vestibular stimulation may entrain endogenous brain rhythms in a target portion of the brain based on the modulated signal.

In some embodiments, the separation in time, S, may be varied according to the formula $S(t)=S_{min}+S_c*\sin(\omega t)$, wherein S(t) is the separation in time, S, between adjacent ones of the plurality of packets of electrical pulses, $S_{min}$ and $S_c$ are time constants, and $\omega$ is proportional to the target stimulus frequency. However, embodiments of the present invention are not limited thereto. For example, in some embodiments, the separation in time, S, may be varied according to other formulas, such as $S(t)=S_{min}+S_c^*\cos(\omega t)$. Without wishing to be bound by any particular theory, it is believed that an amplitude of the separation in time, S, may be inversely proportional to an amplitude of an induced stimulus. For example, with a reduced separation in time, S, a vestibular system will receive more packets of electrical pulses within a given time. Conversely, with an increased separation in time, S, the vestibular system will receive fewer packets of electrical pulses within the given time. By modulating the separation in time, S, an amplitude of the induced stimulus may therefore be modulated. Thus, by modulating the separation in time, S, according to a target frequency, the induced stimulus may therefore be modulated according to the target frequency. Accordingly, brainwaves may be entrained according to the stimulus frequency.

Figure 14:
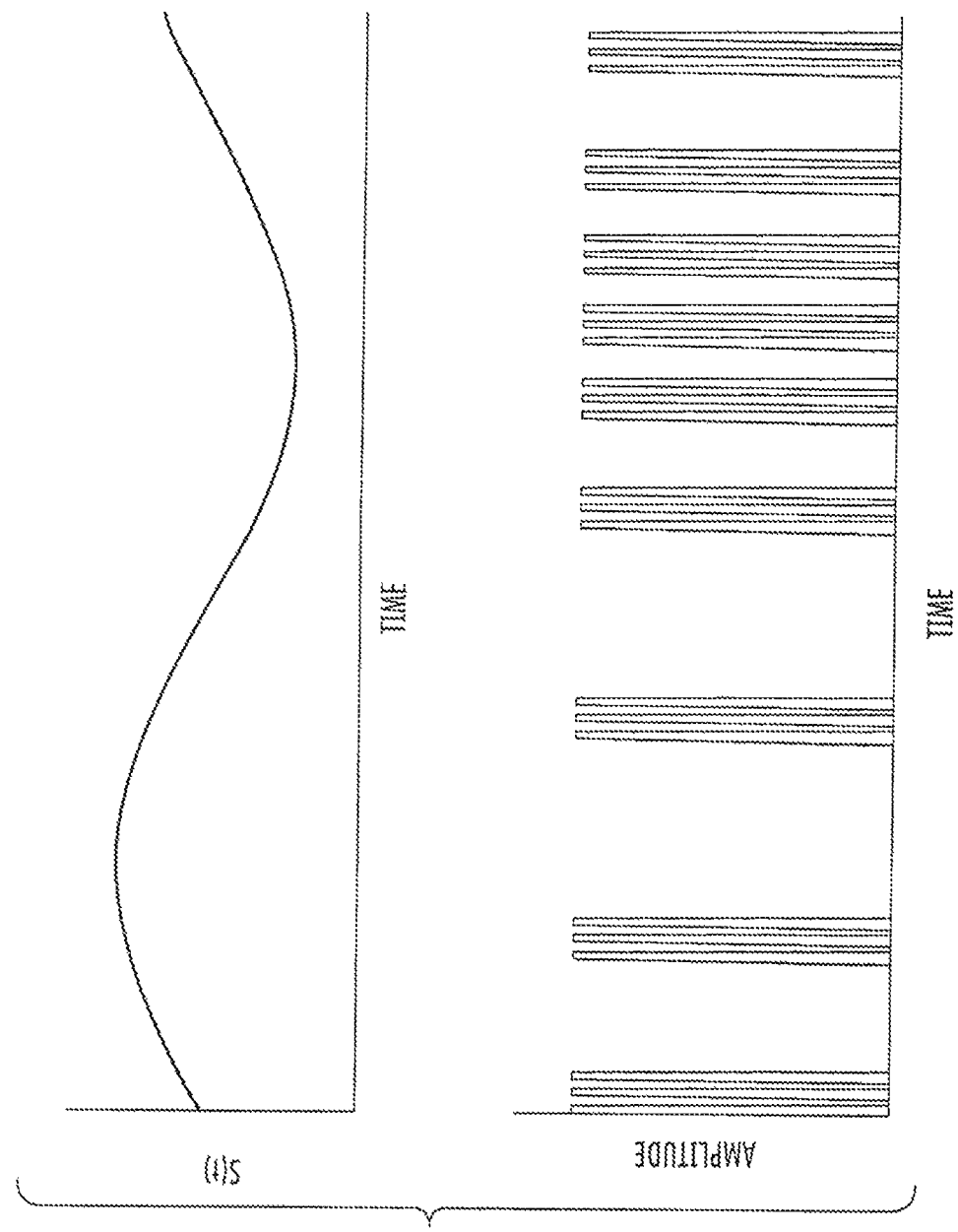
FIG. 14 is a graph illustrating a modulated separation in time between adjacent ones of a plurality of packets of electrical pulses and a corresponding modulated stimulation waveform according to some embodiments of the present invention.

FIG. 14 is a graph illustrating a modulated separation in time between adjacent ones of a plurality of packets of electrical pulses and a corresponding modulated stimulation waveform according to some embodiments of the present invention. Referring to FIG. 14, a separation of time, S, between adjacent ones of a plurality of packets of pulses is illustrated as varied in a sinusoidal modulation. An amplitude of a waveform is illustrated corresponding to the modulation of S. For example, a longer separation in time is illustrated between adjacent packets when S is higher and a shorter separation in time is illustrated when S is lower. In the illustrated example, each of the packets includes three pulses of equal amplitude, width, and separation, however embodiments are not limited thereto.

Figure 15A:
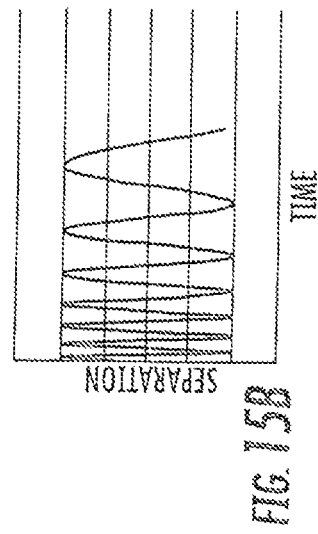
FIGS. 15A, 15C, and 15E are graphs illustrating modulated target stimulus frequencies according to some embodiments of the present invention.
Figure 15C:
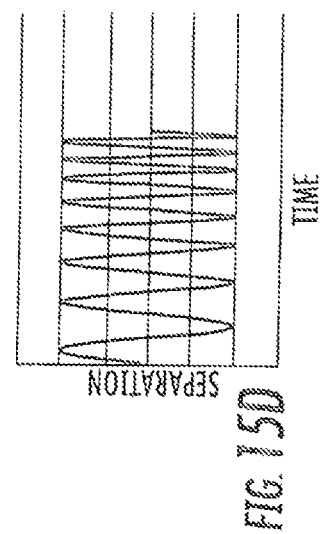
Figure 15E:
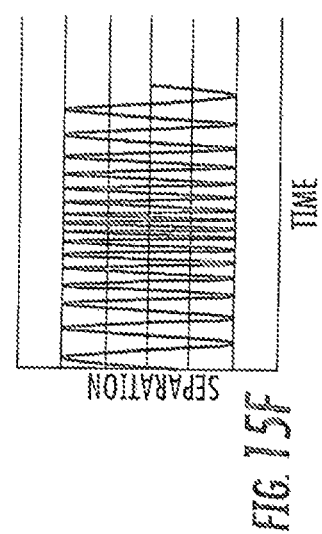
Figure 15B:
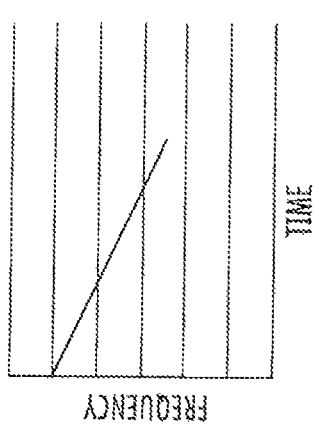
FIGS. 15B, 15D, and 15F are graphs illustrating modulated separations in time between adjacent ones of a plurality of packets of electrical pulses according to the modulated target stimulus frequencies of FIGS. 15A, 15C, and 15E, respectively.
Figure 15D:
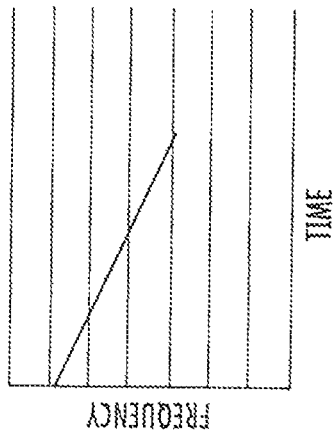
Figure 15F:
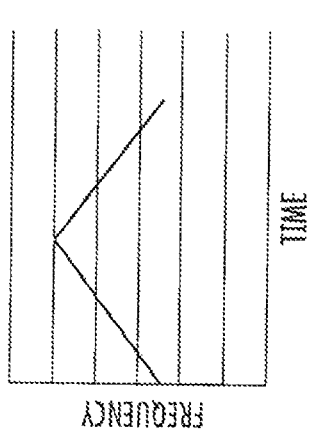

FIGS. 15A, 15C, and 15E are graphs illustrating modulated target stimulus frequencies according to some embodiments of the present invention. FIGS. 15B, 15D, and 15F are graphs illustrating modulated separations in time between adjacent ones of a plurality of packets of electrical pulses according to the modulated target stimulus frequencies of FIGS. 15A, 15C, and 15E, respectively. Referring to FIGS. 12-13 and 15A-15F, in some embodiments, the formula may include more than one target stimulus frequency. For example, in some embodiments, the formula may include a range of frequencies. In some embodiments, the modulating may include modulating the target stimulus frequency between a lower target frequency and a higher target frequency.

Referring to FIGS. 15A-15B, in some embodiments, the modulating may include repeatedly decreasing the target stimulus frequency in a pattern between the higher target frequency and the lower target frequency. A period of the sinusoidal modulation of the separation in time, S, may increase over time as the target frequency decreases. The patterns illustrated in FIGS. 15A-15B may be consecutively repeated for a duration of the galvanic vestibular stimulation.

Referring to FIGS. 15C-15D, in some embodiments, the modulating may include repeatedly increasing the target stimulus frequency in a pattern between the lower target frequency and the higher target frequency. A period of the sinusoidal modulation of the separation in time, S, may decrease over time as the target frequency increases. The patterns illustrated in FIGS. 15C-15D may be consecutively repeated for a duration of the galvanic vestibular stimulation.

Referring to FIGS. 15E-15F, in some embodiments, the modulating may include repeatedly cycling the target stimulus frequency in a pattern of increasing from the lower target frequency to the higher target frequency and then decreasing back to the lower target frequency. A period of the sinusoidal modulation of the separation in time, S, may decrease over time as the target frequency increases and may increase as the target frequency decreases. The patterns illustrated in FIGS. 15E-15F may be consecutively repeated for a duration of the galvanic vestibular stimulation.

Carrier-Based Modulation

Figure 16A:
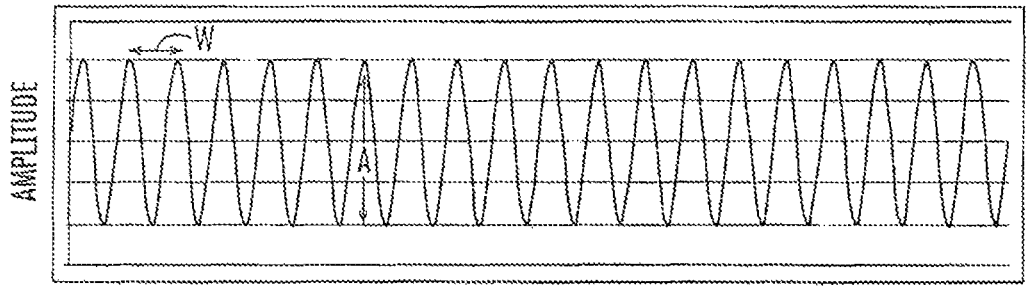
FIGS. 16A-D are graphs illustrating a method for modulating an electrical signal according to some embodiments of the present invention.
Figure 16B:
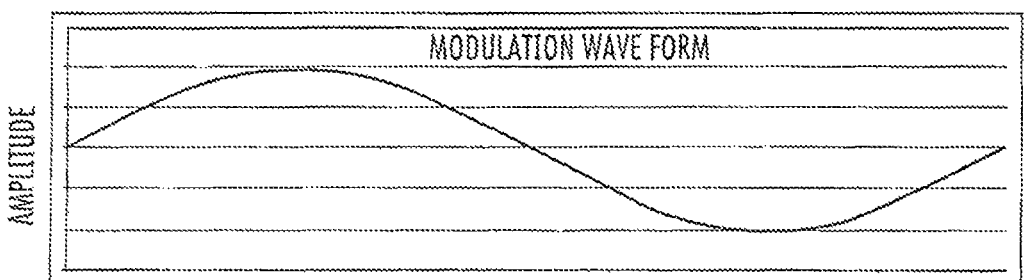
Figure 16C:
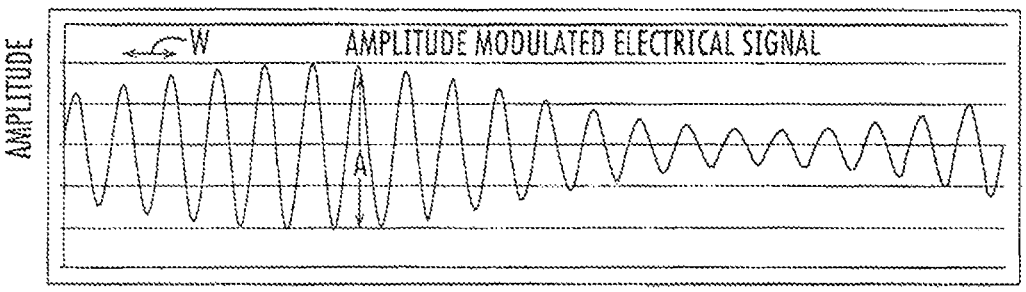
Figure 16D:
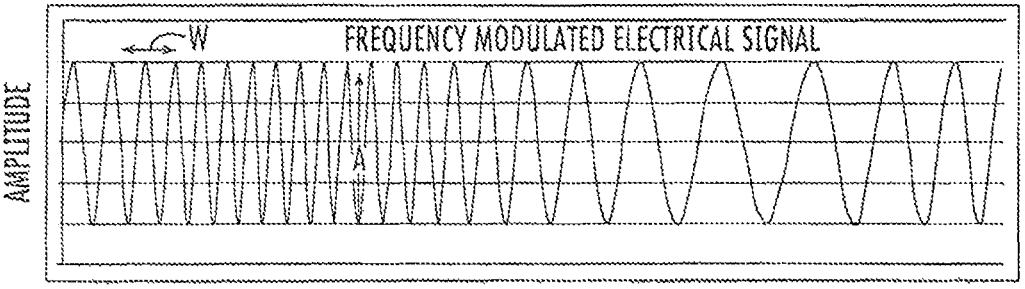

FIGS. 16A-D are graphs illustrating a method for modulating an electrical signal according to some embodiments of the present invention. For example, FIG. 16A is a graph illustrating a carrier waveform function according to some embodiments of the present invention, FIG. 16B is a graph illustrating a modulation waveform according to some embodiments of the present invention, FIG. 16C is a graph illustrating an amplitude modulated electrical signal according to some embodiments of the present invention, and FIG. 16D is a graph illustrating a frequency modulated electrical signal according to some embodiments of the present invention. Referring to FIG. 16A, a carrier waveform function may be a continuous cyclical function. For example, in some embodiments, the carrier waveform function may be a sine wave. In some embodiments, the carrier waveform function may be a square wave, a sawtooth wave, or another waveform function. The carrier waveform function may include an amplitude and a carrier frequency. The carrier waveform function may include a sequence of pulses that may correspond to electrical pulses produced based on the function.

Ones of the pulses may include a width in time, W and an amplitude, A. The width in time, W, of a pulse may be defined as a quantity of time between corresponding phases of adjacent pulses. The amplitude, A, of the waveform may correspond to the amplitude of the voltage and/or current of the electrical signal provided by the electrode 215 of FIG. 8.

An impedance provided by the skin as shown in FIG. 8 in response to an electrical signal corresponding to the carrier waveform function may be based on the width in time, W, of the pulses. For example, the width, W, may define a time period of a pulse. A carrier frequency of the carrier waveform function may be the inverse of the time period. The impedance may be inversely proportional to the frequency of the pulses, as illustrated in FIG. 11. Thus, the width, W, may be selected to be smaller to provide a higher frequency and, thus, a lower impedance. For example, in some embodiments, the carrier frequency may be greater than or equal to about 3 kHz. In some embodiments, the carrier frequency may be about 10 kHz.

Referring to FIGS. 16A-16D, at least one of the amplitude, A, and the carrier frequency may be modulated to modulate a stimulation waveform. The at least one modulated parameter may be modulated based on a time-varying modulation waveform. For example, referring to FIGS. 16A-16C, the amplitude of the carrier waveform function may be modulated based on the modulation waveform to produce an amplitude modulated electrical signal. Referring to FIGS. 16A-16B and FIG. 16D, the frequency of the carrier waveform function may be modulated based on the modulation waveform to produce a frequency modulated electrical signal. In some embodiments, the modulation waveform may be a sinusoidal function. In such embodiments, the amplitude and/or frequency of the carrier waveform function may be varied in a sinusoidal modulation. However, in other embodiments, the modulation waveform may not be sinusoidal and may be another waveform. Referring to FIGS. 8 and 10, the vestibular system may be stimulated based on the modulation frequency. Thus, the modulation frequency may be selected to be low based on the desired diagnostic and/or therapeutic uses of the galvanic vestibular stimulation. In some embodiments, the modulation frequency may be less than about 1 kHz. For example, in some embodiments, the modulation frequency may be between about 0.005 Hz and about 200 Hz. However, in some embodiments, a modulation frequency that is greater than 1 kHz may be selected based on another desired diagnostic and/or therapeutic use of the galvanic vestibular stimulation.

The galvanic vestibular stimulation may have downstream effects in other portions of the brain of the subject based on the modulation frequency. In some embodiments, a frequency of the modulated signal may be selected to induce brain rhythms in a target portion of the brain. In some embodiments, the galvanic vestibular stimulation may entrain endogenous brain rhythms in a target portion of the brain based on the modulated signal.

In some embodiments, the modulation waveform may include more than one modulation frequency. For example, in some embodiments, the modulation waveform may include a range of frequencies. In some embodiments, the modulating may include modulating the modulation waveform between a lower target frequency and a higher target frequency. In some embodiments, the modulating may include repeatedly decreasing the modulation frequency in a pattern between the higher target frequency and the lower target frequency. In some embodiments, the modulating may include repeatedly increasing the modulation frequency in a pattern between the lower target frequency and the higher target frequency. In some embodiments, the modulating may include repeatedly cycling the modulation frequency in a pattern of increasing from the lower target frequency to the higher target frequency and then decreasing back to the lower target frequency.

Applications

Embodiments according to the present invention will now be described with respect to the following non-limiting examples Alteration of Cross-Frequency Coupling The oscillatory activity in multiple frequency bands may be observed in different levels of organization from micro-scale to meso-scale and macro-scale. Studies have been shown that some brain functions are achieved with simultaneous oscillations in different frequency bands. The relation and interaction between oscillations in different bands can be informative in understanding brain function. This interaction between several oscillations is also known as cross-frequency coupling (CFC).

Two forms of recognized CFC in brain rhythms are: phase amplitude coupling (PAC), and phase-phase coupling (PPC). In phase amplitude coupling, the phase of the lower frequency oscillation may drive the power of the coupled higher frequency oscillation, which may result in synchronization of amplitude envelope of faster rhythms with the phase of slower rhythms. Phase-phase coupling is amplitude independent phase locking between high and low frequency oscillation.

It is believed that phase-amplitude coupling may be a mechanism for communication within and between distinct regions of the brain by coordinating the timing of neuronal activity in brain networks. That brain rhythms modulate the excitability of neuronal ensembles through fluctuations in membrane potentials, biasing the probability of neuronal spiking at a specific phase of the slower rhythm. PAC is thought to dynamically link functionally related cortical areas that are essential for task performance.

Parkinson's disease (PD) has been shown to be associated with exaggerated coupling between the phase of beta oscillations and the amplitude of broadband activity in the primary motor cortex, likely constraining cortical neuronal activity in an inflexible pattern whose consequence is bradykinesia and rigidity. See, e.g., C. de Hemptinne, N. C. Swann, J. L. Ostrem, E. S. Ryapolova-Webb, M. San Luciano, N. B. Galifianakis, P. A. Starr, Therapeutic deep brain stimulation reduces cortical phase-amplitude coupling in Parkinson's disease, *Nat Neurosci* 18, 779-786 (2015); published online EpubApr 13 (10.1038/nn.3997). Parkinson's disease may be associated with a range of symptoms that originate, or are centered, in different brain regions. It is believed that aberrant cross-frequency coupling between two different EEG bands may be present when a patient experiences tremor. It is believed that CVS and/or GVS may be used to alter the cross-frequency coupling so as to renormalize function and re-establish proper balance.

Stimulation of a region in the brain stem called the PPN has been shown to improve, for example, the normalization of gait in PD patients. See, e.g., H. Morita, C. J. Hass, E. Moro, A. Sudhyadhom, R. Kumar, M. S. Okun, Pedunculopontine Nucleus Stimulation: Where are We Now and What Needs to be Done to Move the Field Forward? *Front Neurol* 5, 243 (2014); published online (10.3389/fneur.2014.00243). With respect to the present invention, without wishing to be bound by theory, it is believed that vestibular stimulation may modulate activity of the PPN. For example, CVS may be used to stimulate the PPN. In some embodiments, GVS may be used to break up the aberrant cross frequency coupling associated with tremor simultaneous with the use of CVS to stimulate the PPN. Thus, the two modalities may modulate different brain regions to improve the efficacy of the treatment.

More generally, GVS may be used to sensitize or give preference to a subset of neural pathways that respond to a specific excitation frequency (for example, within the EEG bands), making them more responsive to CVS neuromodulation. These selected pathways would then be subject to differential modulation in the background of other, non-selected pathways. An illustrative example would be the use of GVS in the theta band frequency range, associated with hippocampal activity, to sensitize pathways associated with memory encoding. GVS at a sub-threshold intensity may be used, or the intensity may be above the activation threshold of the afferent vestibular nerves. The CVS waveform would be chosen so as to overlap and enhance the neuromodulatory effects of the targeted GVS modulation.

Controlling IGF-1 Accretion

Insulin-like growth factor 1 (IGF-1) is a hormone that is similar in molecular structure to insulin that is believed to play an important role in childhood growth and to have anabolic effects in adults. The protein is encoded in humans by the IGF1 gene. It is believed that IGF-1 may also provide mitochondrial protection Insulin-like growth factor number one (IGF-1) is a hormone (MW: 7649 daltons) similar in molecular structure to insulin. It plays an important role in childhood growth and continues to have anabolic effects in adults. Its production is encoded by the IGF1 gene and it is produced primarily in the liver as an endocrine hormone, though production in the central nervous system has also been observed. In circulation, IGF-1 is bound to one of six proteins, the most common being IGFBP-3. These chaperone proteins increase the half life of IGF-1 in circulation from around 15 minutes (unbound) to 15 hours (bound). IGF-1 production is associated with growth hormone (GH) and blood tests for GH use IGF-1 as a surrogate, since the concentration of the latter tends not to vary as much over a daily cycle as that of GH does. IGF-1 is one of the most potent natural activators of the AKT signaling pathway, a stimulator of cell growth and proliferation, and a potent inhibitor of programmed cell death. It protects and strengthens cells at one of their most vulnerable moments, when they are in the process of and immediately after dividing. It is believed that IGF-1 may provide mitochondrial protection from mitochondrial stress.

Electrical stimulation of the fastigial nucleus (FN) for a sufficient time and at the right frequency has been shown to lead to neuroprotection via reduction of apoptosis in mitochondria in the ischemic area. See, e.g., P. Zhou, L. Qian, T. Zhou, C. Iadecola, Mitochondria are involved in the neurogenic neuroprotection conferred by stimulation of cerebellar fastigial nucleus, *J Neurochem* 95, 221-229 (2005). It is believed that IGF-1 may be a factor in such neuroprotection. Electrical stimulation has been shown to result in the recruitment of IGF-1 from systemic circulation, through the blood-brain-barrier, and to very localized usage by or around the point of the stimulated nerves. Effectively, the nerve activity signaled for and recruited IGF-1. See, e.g., T. Nishijima, J. Piriz, S. Duflot, A. M. Fernandez, G. Gaitan, U. Gomez-Pinedo, J. M. Verdugo, F. Leroy, H. Soya, A. Nunez, I. Torres-Aleman, Neuronal activity drives localized blood-brain-barrier transport of serum insulin-like growth factor-I into the CNS, *Neuron* 67, 834-846 (2010). It is believed that vestibular stimulation may similarly accomplish the recruitment of and/or enhance the efficiency of IGF-1, either directly affecting nerves active during vestibular stimulation or possibly nearby nerves receive IGF-1 in a bystander effect. For migraine headache in particular, increased rCBF may be a key factor enabling increased IGF-1 uptake through the BBB. Mechanisms for altering blood flow mesh nicely with existing observations/beliefs around the etiology of migraines. That IGF-1 also facilitates synaptic plasticity could mean it has a role in mitigating central pain associated with chronic migraines.

With respect to the present invention, without wishing to be bound by theory, it is believed that vestibular stimulation, or in particular CVS and/or GVS, may be used to increase IGF-1 transport across the blood-brain-barrier, and therefore increase mitochondrial protection, in frequency-dependent targeted regions of the central nervous system. In some embodiments, CVS and GVS may be combined. For example, CVS may be used to provide stimulation of frequency-dependent regions of the brain and GVS may be used to provide neuroprotection to the stimulated regions and/or surrounding regions.

Although embodiments have been described with reference to galvanic vestibular stimulation through an ear canal, the present inventive concepts are not limited thereto. For example, in some embodiments, the vestibular system may be stimulated through at least one electrode in contact with a portion of the skin behind the ear in proximity to a mastoid part of a temporal bone. In some embodiments, delivering the electrical signal may include transdermal electrical stimulation of other portions of a nervous system of the subject. In some embodiments, the described modulation scheme may be used with implantable electrodes or other devices that do not stimulate through the skin.

Audio Waveforms

In some embodiments, neurostimulation may be performed based on an audio waveform. For example, a time-varying modulation waveform used for modulating an electrical signal that is delivered to a patient may be an audio waveform. As used herein, an audio waveform is a waveform that includes frequency components that are within a hearing range of the subject. For example, an audio waveform may include frequency components within a range of about 20 to 20,000 Hz. In some embodiments, the audio waveform may be time-varying and/or may include one or more patterns. For example, the audio waveforms may include music and/or voice. In some embodiments the audio waveforms may include sounds of an environment, such as the sounds of rain, birds, moving water, cars, etc. In some embodiments, the audio waveforms may be based on audio recordings. In some embodiments, the waveforms of the galvanic vestibular stimulation may be modulated based on the audio waveforms.

As used herein, modulation of an electrical signal based on an audio waveform means that the frequency components of the audio waveform within a hearing range of the subject are encoded into the electrical signal. For example, notes or sounds that are in the audio waveform may be encoded into the electrical signal. In some embodiments, the electrical signal may include a carrier waveform at a frequency that is at least twice a highest frequency of the frequency components of the audio waveform encoded into the electrical signal. The audio waveform may be encoded into the carrier waveform via, for example, frequency or amplitude modulation. In some embodiments, an electrical signal may not be referred to as being modulated based on the audio waveform if the electrical signal is modulated based on beats or other features of the audio waveform in the absence of the frequency components of the audio waveform that are within the hearing range of the subject.

Combination of CVS and GVS to Enhance IGF-1 Delivery

As discussed in more detail below, in some embodiments, a combination of CVS and GVS may be used to activate a neuroprotective function. For example, without wishing to be bound by any particular theory, apoptosis in mitochondria may be reduced through neurostimulation by increasing IGF-1 uptake through a blood-brain-barrier by inducing oscillations in cerebral blood flow.

Figure 18:
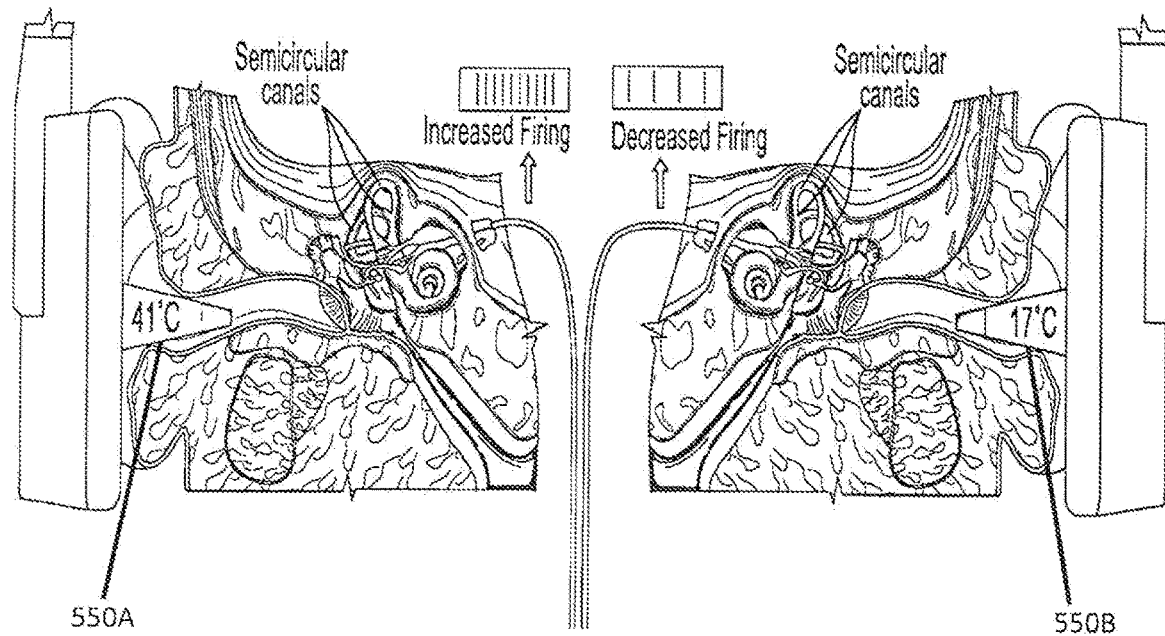
FIG. 18 is a cross-sectional view schematically illustrating an effect of CVS on vestibular nerves according to some embodiments of the inventive concepts.

FIG. 18 is a cross-sectional view schematically illustrating an effect of CVS on vestibular nerves according to some embodiments of the inventive concepts. Referring to FIG. 18, administration of CVS may include raising and/or lowering temperatures of the earpieces 550A, 550B. For example, in some embodiments, as illustrated in FIG. 18, the temperature of earpiece 550A may be controlled to a higher temperature while the earpiece 550B may be controlled to a lower temperature. Regular neurons have an equilibrium firing rate of about 100 Hz. Lowering the temperature of the regular neurons may lower the firing rate of the neurons and increasing the temperature of the neurons may increase the firing rate of the neurons. Accordingly, the temperatures of the earpieces 550A, 550B may be controlled to alter the firing rate of neurons in the respective ears corresponding to a CVS waveform. The period of a CVS waveform may be limited by the thermal conduction time of the temporal bone. However, the actual firing pattern created by time-varying CVS in the vestibular nuclei may be complex. A temperature ramp may create an increasing or decreasing frequency signal, often termed a "chirp." Thus, even though the frequency of a CVS thermal waveform is significantly less than 1 Hz, the induced firing rate may extend for many 10's of Hz above and/or below the equilibrium firing rate. Furthermore, each ear may be stimulated independently, leading to a highly complex frequency modulation space in the brainstem.

Figure 19:
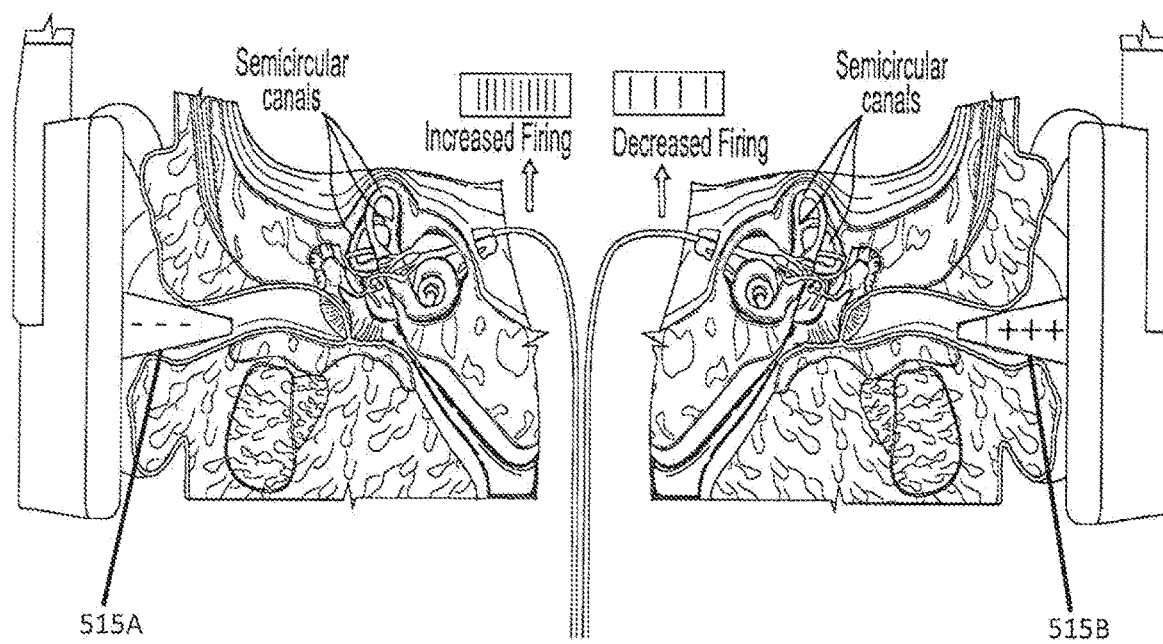
FIG. 19 is a cross-sectional view schematically illustrating an effect of GVS on vestibular nerves according to some embodiments of the inventive concepts.

FIG. 19 is a cross-sectional view schematically illustrating an effect of GVS on vestibular nerves according to some embodiments of the inventive concepts. Referring to FIG. 19, administration of GVS may include providing modulated voltage and/or current to the electrodes 515A, 515B. For example, in some embodiments, as illustrated in FIG. 19, a negative voltage/current may be applied to the electrode 515A and a positive voltage/current may be applied to the electrode 515B. The negative voltage/current may increase the firing rate of the neurons and the positive voltage/current may lower the firing rate of the neurons. Accordingly, the modulated voltage and/or current applied to the electrodes 515A, 515B may be controlled to alter the firing rate of neurons in the respective ears corresponding to a modulated GVS waveform.

Figure 20:
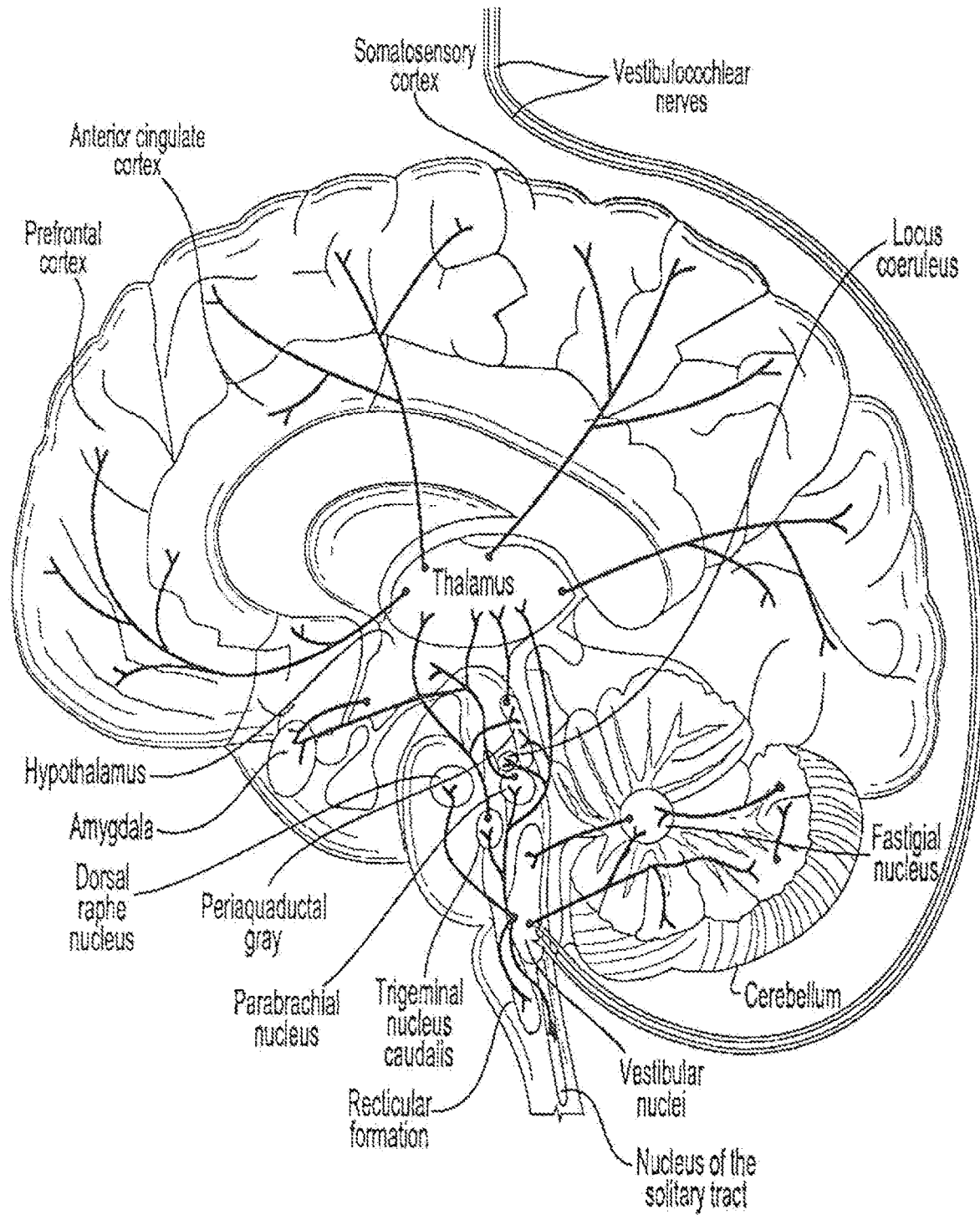
FIG. 20 is a cross-sectional view schematically illustrating an effect of vestibular neurostimulation on a brain according to some embodiments of the inventive concepts.

FIG. 20 is a cross-sectional view schematically illustrating an effect of vestibular neurostimulation on a brain according to some embodiments of the inventive concepts. FIG. 20 illustrates a map of some brain regions (particularly relevant to migraine headache) that may be innervated by the vestibular system. Via thalamic relays, the vestibular system may exert control on other sensory cortices. For example, information en route to the cerebral cortex may first pass through the thalamus. However, a long-held view that the thalamus serves as a simple high fidelity relay station for sensory information to the cortex has over recent years been dispelled. There are multiple projections from the vestibular nuclei to thalamic nuclei, including the ventrobasal nuclei, and the geniculate bodies, regions typically associated with other modalities. Further, some thalamic neurons have been shown to respond to stimuli presented from across sensory modalities. For example, neurons in the anterodorsal and laterodorsal nuclei of the thalamus may respond to visual, vestibular, proprioceptive and somatosensory stimuli and integrate this information to compute heading within the environment. Therefore, the thalamus may serve crucial integrative functions, at least in regard to vestibular processing, beyond that imparted by a "simple" relay. Accordingly, a vestibular neuromodulation waveform may be relayed to target portions of the brain and may entrain brain waves at a target frequency.

In mammals there are generally two types of vestibular hair cells, Type I hair cells and Type II hair cells. Each of these classes of hair cells has a distinctive pattern of afferent ending onto the hair cell. One important factor that varies between the different afferents is the regularity of the afferent's resting discharge rate. Afferents that are innervated only by type I hair cells have action potentials that generally fire at very irregular rates when firing spontaneously. Afferents that are innervated only by type II hair cells generally have very regular static discharge rates.

GVS may preferentially affect irregularly firing hair cells within the vestibular receptor organs. Further, GVS may affect hair cells in all of the semicircular canals and otoliths (not a subset). Cathodal (DC) GVS may increase afferent firing rate whereas anodal GVS may decrease the firing rate. This is analogous to an increase in firing rate associated with warm CVS (that is, above body temperature) and a decrease with cold CVS. Irregularly firing hair cells comprise roughly 25% of the afferent output of the vestibular organs.

CVS may be capable of activating both regularly and irregularly firing hair cells. Regular hair cells fire at approximately 100 Hz in equilibrium and CVS may alter firing rate around this value. A rapid temperature change may engage irregularly firing hair cells as well. Whereas the horizontal semicircular canal is generally described as the principal target of CVS, the other canals and otoliths may also respond.

Therefore, CVS may affect regularly and irregularly firing hair cells in all of the vestibular sensing organs, whereas GVS primarily affects the irregularly firing hair cells in all of the vestibular sensing organs. Accordingly, CVS and GVS activation patterns may not be identical.

Irregularly firing hair cells may have evolved with amniotes in order to facilitate vestibular tracking of higher frequency movements. For example, land animals developed necks and this new degree of freedom may have necessitated a faster-responding hair cell type (irregular). So-called head direction cells have been identified in the hippocampal complex and this type of sensory cell may rely on irregularly firing vestibular hair cells to properly provide feedback on the position of the body in space. Across different species of mammals, there is a substantial constancy of the linear dimensions of the respective vestibular organs. Across seven orders of magnitude in size, the physical dimensions of the semicircular canals may vary by less than one order of magnitude. This level of evolutionary conservancy in vestibular organs attributes may be evidence of a high significance of a change in basic vestibular function, such as the emergence of irregularly firing hair cells.

Borrowing from a development in optics and visual processing, spatial frequency analysis, it may be possible to characterize an image by separating high and low spatial frequencies. High spatial frequencies are necessary to encode edges and sharp changes in contrast. Low spatial frequencies capture general shape and general contrast. The visual system in mammals may segregate raw input from the retina, with some cortical regions responding to edges, contrast changes, etc. In other words, the visual cortex may perform operations analogous to a spatial frequency decomposition on raw sensory flow from the retina. The processing of visual images has been studied in terms of areas in the visual cortex that respond to rapid or less rapid changes in image contrast over a given length scale, so-called high and low spatial frequencies respectively. The brain may unit the different spatial frequency regimes into a coherent whole, but may also utilize the two domains individually for some processing tasks.

This result may be generalized to other sensory modalities, like the vestibular system. The vestibular system has fast-responding (irregular) and more slowly responding (regular) hair cells that may characterize movement. The brain's overall perception of movement may be informed by the integration of both movement categories. The output of the irregularly firing hair cells may contribute to excitation at high frequencies and, therefore, GVS stimulation may primarily contribute to excitation at high frequencies. Slowly changing temperatures delivered by CVS may primarily affect regularly firing hair cells and may provide higher information density in the lower spatial frequencies. Therefore, it may be possible to utilize CVS and GVS in combination to affect different ends of the frequency spectrum of vestibular sensory flow. Regular and irregular vestibular outputs may innervate the same brain regions (that is, the two components don't have divergent pathways), but the information content may be different and may enable different outcomes in terms of cognitive or behavioral states. As a specific example, the irregularly firing hair cells may have evolved specifically because new behavioral abilities of land animals were not being well-encoded by regular hair cells alone.

As discussed above, electrical stimulation of the fastigial nucleus (FN) for a sufficient time and at the right frequency has been shown to lead to neuroprotection via reduction of apoptosis in mitochondria in the ischemic area. More specifically, electrical stimulation of the FN may reduce the release of cytochrome-c from mitochondria. Cytochrome-c release is part of the apoptotic chain. The neuroprotective effect may be frequency dependent and a minimum duration of stimulation may be needed to provide neuroprotection.

IGF-1 may inhibit cytochrome-c release from mitochondria. Passage of IGF-1 through the blood-brain-barrier may occur in response to specific signaling in the brain and may be facilitated by enhancement of neurovascular coupling by increase blood flow. This effect may also be frequency dependent.

Stimulation of the FN may lead to changes in cerebral blood flow (CBF). This may be important in facilitating the signaling in the brain to activate passage of IGF-1 though the blood-brain-barrier. Time-varying CVS may induce oscillations in CBF. Therefore, vestibular stimulation may be used to activate the FN, which may induce oscillations in CBF, which may activate passage of IGF-1 through the blood-brain-barrier, which may protect mitochondria against apoptotic death, promote synaptogenesis, and/or improve neurovascular coupling, thus providing neuroprotective effects. For example, IGF-1 may inhibit cytochrome-c release from mitochondria, which may reduce apoptosis in mitochondria. This may be an innate response that protects neurons in the brain. Accordingly, time-varying CVS and/or GVS may be used to activate this innate protective mode.

The impact of vestibular stimulation on IGF-1 movement may be dependent on a time-varying aspect of the CVS and/or GVS. For example, time-varying CVS may leads to oscillations in CBF. In some embodiments, stimulation waveforms may be selected that facilitate the production of CBF oscillations. For example, the CBF oscillations may be measured using, for example, transcranial Doppler sonography. Accordingly, a plurality of stimulation waveforms may be sequentially tried while measuring for CBF oscillations. One or more waveforms that produce desired CBF oscillations may be selected. This may be done with a patient at a start of a therapy to optimize the waveform choice that provides the most effective amount of CBF oscillations.

In some embodiments, time-varying CVS may be used to excite CBF oscillations while using a narrow frequency GVS to select a subset of brain regions to activate, thus facilitating the movement of IGF-1 across the BBB. The time-varying CVS and the narrow-frequency GVS may both work to increase IGF-1 uptake through the blood-brain-barrier.

In some embodiments, a positron-emitting radionuclide may be used as a Positron Emission Tomography (PET) label on IGF-1. The PET label may be introduced systemically while measuring uptake in the brain via PET imaging. Accordingly, it may be seen where IGF-1 uptake increases based on the type of vestibular neurostimulation applied. In some embodiments, the positron-emitting radionuclide may be a PET label on glucose or oxygen to detect blood flow. For example, some embodiments may use fluorine-18 labeled fluorodeoxyglucose or oxygen-15. In some embodiments, transcranial Doppler sonography to measure the induction of cerebral blood flow oscillations. In some embodiments, CBF oscillations may be measured via transcranial Doppler sonography while sequentially trying a plurality of stimulation waveforms to select one or more waveforms that produce desired CBF oscillations, as described above, at a start of a therapy to optimize the waveform choice that provides the most effective amount of CBF oscillations. In some embodiments, the transcranial Doppler sonography may be used to compare before and during vestibular neuromodulation to identify differences in PET uptake to hone in on regions where additional IGF-1 has entered the central nervous system due to the vestibular neuromodulation.

As an example, cerebral blood flow oscillations may include B waves. B waves are spontaneous oscillations in cerebral blood flow velocity (CBFv) that may have a frequency of about 0.5 to about 3 cycles per minute, thus a period of about 20 seconds to about 2 minutes. There is experimental evidence that B waves may be due to fluctuations in vessel diameters triggered by monoaminergic and serotonergic centers in the midbrain and pons. B waves may be part of an autoregulatory response and their average period may to correspond to a complete cycle time for blood moving from the heart to the brain and back. Some studies have shown a correlation between abnormal B wave activity and migraine headaches, that period leg movements (also called restless leg syndrome) may be part of a common endogenous rhythm matching the B wave period, and that B waves may be more prominent in NREM sleep. B waves may be a significant predictor of survival after traumatic brain injury.

The B wave period may fall in a range found in functional connectivity studies of the sensory cortices. Functional connectivity in the auditory, visual, and sensorimotor cortices may be significantly characterized by frequencies slower than those in the cardiac and respiratory cycles. In functionally connected regions, these low frequencies may be characterized by a high degree of temporal coherence. This functional connectivity may have the same pacing *nexus* that gives rise to B waves, which may indicate neurovascular coupling. Thus, the entrainment of B waves may also entrain the above describe sensory functional connectivity.

For example, time-varying CVS may induce significant oscillations in the Gosling Pulsatility Index (PI), which is a measure of cerebrovascular resistance defined as [(peak systolic velocity–end diastolic velocity)/mean cerebral blood flow velocity], a primary measure of cerebrovascular dynamics. A time-varying CVS treatment may induce PI spectral peaks at intervals that may fall within the periodicity range of B waves and may not match periods of the warm and cold waveforms. Studies have provided evidence for a monoaminergic B-wave pacing center in the pons, an area that receives direct innervation from the vestibular nuclei in the brainstem, which may be how the time-varying CVS treatment may induce oscillations. In other words, the time-varying CVS may entrain the pontine structures responsible for B-wave pacing, as evidenced by a significant increase of spectral power at spectral frequencies within the range of B-waves in a post-CVS period.

CVS and GVS Co-Neuromodulation

As used herein, the terms "vestibular neuromodulation" and "vestibular neurostimulation" may each refer to the stimulation of the vestibular nerve, which may include CVS and/or GVS.

Methods of treating a patient using neuromodulation may include a combination of CVS and GVS that are applied together. For example, in some embodiments, the CVS and GVS may be applied simultaneously. The CVS and GVS may each include a time-varying stimulation waveform. As used herein, stimulations may be considered to be applied simultaneously when applied as part of a single treatment. For example, in some embodiments, the CVS and GVS may be applied simultaneously when applied within an hour of each other as measured from the end of the first to the beginning of the second. In some embodiments, the CVS and GVS may be applied simultaneously when applied within an thirty minutes of each other, or fifteen minutes, or five minutes. In some embodiments, the CVS and GVS may be applied simultaneously when there is an overlap in time between the application of the CVS and the application of the GVS.

In some embodiments, the CVS and GVS may excite different frequencies in the brain. For example, the CVS may be used to excite frequencies less than 1 Hz. The GVS may be used to excite frequencies greater than 1 Hz. In some embodiments, the GVS may be used to excite frequencies between about 0.005 Hz and about 200 Hz and may be different than a frequency of the CVS. In some embodiments, frequencies of the GVS may be at least a multiple of a maximum frequency of the CVS. For example, the frequencies of the GVS may be at least 10 times a maximum frequency of the CVS.

In some embodiments, there may be a defined phase difference between the stimulation waveform of the CVS and the stimulation waveform of the GVS. For example, the stimulation waveform of the CVS and the stimulation waveform of the GVS may be controlled to maintain a 180° phase difference. Accordingly, the GVS may suppress an irregular hair cell contribution of the net applied vestibular neuromodulation. Therefore, a net applied vestibular neuromodulation may be controlled to affect mainly regular firing hair cells, mainly irregular firing hair cells, or a mixture of regular and irregular firing hair cells.

In some embodiments, a small relative frequency difference between the stimulation waveform of the CVS and the stimulation waveform of the GVS may result in a net effect at a beat frequency. The beat frequency may be equal to the difference between the stimulation waveform of the CVS and the stimulation waveform of the GVS. For example, a target frequency may be selected for a desired effect in a treatment. The stimulation frequency of the CVS and the stimulation frequency of the GVS may each be controlled to have a difference equal to the desired target frequency. One or more of the stimulation waveform of the CVS and the stimulation waveform of the GVS may be modulated to vary the target frequency.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A vestibular neurostimulation device, comprising:
    first and second electrodes;
    first and second thermoelectric devices thermally coupled, respectively, to first and second earpieces configured to be insertable into respective ear canals of a patient; and
    a controller comprising a waveform generator that is configured to deliver a modulated electric signal to the patient through galvanic vestibular stimulation (GVS) using the first and second electrodes and to deliver a time varying thermal waveform to the patient through caloric vestibular stimulation (CVS) using the first and second earpieces simultaneous with the delivery of the modulated electrical signal through GVS,
    wherein the CVS and/or GVS is configured to increase a passage of insulin-like growth factor 1 (IGF-1) through a blood-brain-barrier.

2. The neurostimulation device of claim 1, wherein the first and second earpieces comprise the first and second electrodes, respectively.

3. The neurostimulation device of claim 1, wherein the modulated electrical signal is configured to excite different frequencies than the time varying thermal waveform.

4. The neurostimulation device of claim 3,
    wherein the modulated electrical signal is configured to excite frequencies greater than 1 Hz, and
    wherein the time varying thermal waveform is configured to excite frequencies less than 1 Hz.

5. The neurostimulation device of claim 3, wherein the modulated electrical signal is configured to excite frequencies that are at least 10 times greater than a maximum of frequencies that the time varying thermal waveform is configured to excite.

6. The neurostimulation device of claim 1, wherein the controller is configured to control the modulated electrical signal and the time varying thermal waveform to maintain a defined phase difference between the modulated electrical signal and the time varying thermal waveform.

7. The neurostimulation device of claim 6, wherein the controller is configured to control the modulated electrical signal to be approximately 180° out of phase with the time varying thermal waveform.

8. The neurostimulation device of claim 1, wherein the controller is configured to producing a net stimulation at a beat frequency equal to a difference between a frequency of the modulated electrical signal and a frequency of the time varying thermal waveform by controlling the frequency of the modulated electrical signal relative to the frequency of the time varying thermal waveform.

9. The neurostimulation device of claim 1, wherein the CVS is configured to produce oscillations in a cerebral blood flow.

10. The neurostimulation device of claim 9, wherein the time varying thermal waveform is configured to facilitate production of the oscillations in the cerebral blood flow.

11. The neurostimulation device of claim 10,
    wherein the controller is configured to sequentially apply a plurality of time varying thermal waveforms, measure respective cerebral blood flow oscillations resulting from the plurality of time varying thermal waveforms, and select at least one of the plurality of time varying thermal waveforms that produces an effective amplitude of cerebral blood flow oscillations, and
    wherein the controller is configured to deliver the time varying thermal waveform to the patient through CVS simultaneous with the delivery of the modulated electrical signal through GVS by delivering the selected at least one of the plurality of time varying thermal waveforms.

12. The neurostimulation device of claim 11, wherein the modulated electrical signal is configured to activate a subset of brain regions for the increase in passage of IGF-1 through the blood-brain-barrier.

13. The neurostimulation device of claim 1, wherein the modulated electrical signal and/or the time varying thermal waveform are configured to reduce symptoms of a neurological disease.

14. The neurostimulation device of claim 1, wherein the modulated electrical signal and/or the time varying thermal waveform are configured to reduce symptoms of Parkinson's disease.

15. The neurostimulation device of claim 1, wherein the modulated electrical signal and/or the time varying thermal waveform are configured to reduce symptoms of migraine headache.

16. A vestibular neurostimulation device, comprising:
first and second electrodes;
first and second thermoelectric devices thermally coupled, respectively, to first and second earpieces configured to be insertable into respective ear canals of a patient; and
a controller comprising a waveform generator that is configured to deliver a modulated electric signal to the patient through galvanic vestibular stimulation (GVS) using the first and second electrodes and to deliver a time varying thermal waveform to the patient through caloric vestibular stimulation (CVS) using the first and second earpieces simultaneous with the delivery of the modulated electrical signal through GVS,
wherein the modulated electrical signal is configured to activate a subset of brain regions for an increase in passage of insulin-like growth factor 1 (IGF-1) through a blood-brain-barrier.

17. The neurostimulation device of claim 16, wherein the modulated electrical signal and/or the time varying thermal waveform are configured to reduce symptoms of a neurological disease.

18. The neurostimulation device of claim 16, wherein the modulated electrical signal and/or the time varying thermal waveform are configured to reduce symptoms of Parkinson's disease.

19. The neurostimulation device of claim 16, wherein the modulated electrical signal and/or the time varying thermal waveform are configured to reduce symptoms of migraine headache.

20. The neurostimulation device of claim 16, wherein the CVS is configured to produce oscillations in a cerebral blood flow.

* * * * *